US011369809B2

(12) United States Patent
Goetz et al.

(10) Patent No.: US 11,369,809 B2
(45) Date of Patent: Jun. 28, 2022

(54) NEURODEGENERATIVE DISEASE TREATMENT

(71) Applicant: THE UNIVERSITY OF QUEENSLAND, St Lucia (AU)

(72) Inventors: Juergen Goetz, St Lucia (AU); Gerhard Leinenga, St Lucia (AU)

(73) Assignee: THE UNIVERSITY OF QUEENSLAND, Queensland (AU)

( * ) Notice: Subject to any disclaimer, the term of this patent is extended or adjusted under 35 U.S.C. 154(b) by 712 days.

(21) Appl. No.: 15/320,578

(22) PCT Filed: Jun. 19, 2015

(86) PCT No.: PCT/AU2015/050345
§ 371 (c)(1),
(2) Date: Dec. 20, 2016

(87) PCT Pub. No.: WO2015/192189
PCT Pub. Date: Dec. 23, 2015

(65) Prior Publication Data
US 2018/0214716 A1 Aug. 2, 2018

(30) Foreign Application Priority Data
Jun. 20, 2014 (AU) ............................... 2014902366

(51) Int. Cl.
*A61N 7/00* (2006.01)

(52) U.S. Cl.
CPC ........ *A61N 7/00* (2013.01); *A61N 2007/0026* (2013.01); *A61N 2007/0039* (2013.01); *A61N 2007/0078* (2013.01); *A61N 2007/0082* (2013.01)

(58) Field of Classification Search
CPC .............. A61N 7/00; A61N 2007/0078; A61N 2007/0039; A61N 2007/0026; A61N 2007/0082
See application file for complete search history.

(56) References Cited

U.S. PATENT DOCUMENTS 6,514,221 B2  2/2003  Hynynen et al.
6,612,988 B2  9/2003  Maor et al.
(Continued)

FOREIGN PATENT DOCUMENTS

CN    106215336    12/2016
EP       2496307     1/2016
(Continued)

OTHER PUBLICATIONS

Jordão, Jessica F., et al. "Amyloid-β plaque reduction, endogenous antibody delivery and glial activation by brain-targeted, transcranial focused ultrasound."  Experimental neurology  248 (2013): 16-29. (Year: 2013).*

(Continued)

*Primary Examiner* — Sean D Mattson
(74) *Attorney, Agent, or Firm* — Foley & Lardner LLP

(57) ABSTRACT

The present invention is directed to methods for treating neurodegenerative diseases and/or improving cognitive function, in particular those associated with protein oligomers, aggregates or deposits, using acoustic energy, such as ultrasound. An 5 example of such a neurodegenerative disease is Alzheimer's disease. The present invention provides a method of improving cognitive function and/or memory in an individual with impaired memory and/or executive function, the method including the steps of identifying a region of the brain of the individual to be treated with acoustic energy, applying a clinically safe level of acoustic energy to the region, thereby 10 saturating or substantially saturating the region with acoustic energy, thereby improving memory in the individual.

36 Claims, 11 Drawing Sheets

(56) References Cited

U.S. PATENT DOCUMENTS

| | | |
|---|---|---|
| 7,674,229 B2 | 3/2010 | Hynynen et al. |
| 8,353,853 B1 | 1/2013 | Kyle et al. |
| 9,302,124 B2 | 4/2016 | Konofagou et al. |
| 9,358,023 B2 | 6/2016 | Konofagou et al. |
| 9,403,038 B2 | 8/2016 | Tyler |
| 9,737,698 B2 | 8/2017 | Topchiashvili et al. |
| 2002/0038086 A1* | 3/2002 | Hynynen .......... A61M 37/0092 600/431 |
| 2004/0049134 A1 | 3/2004 | Tosaya et al. |
| 2005/0020945 A1 | 1/2005 | Tosaya et al. |
| 2009/0005711 A1* | 1/2009 | Konofagou ....... A61M 37/0092 601/2 |
| 2010/0143241 A1* | 6/2010 | Johnson ............. A61K 41/0028 424/1.11 |
| 2012/0289869 A1 | 11/2012 | Tyler |
| 2012/0296241 A1 | 11/2012 | Mishelevich |
| 2013/0281890 A1 | 10/2013 | Mishelevich |
| 2015/0045724 A1 | 2/2015 | Chen et al. |
| 2016/0243381 A1 | 8/2016 | Alford et al. |
| 2017/0246481 A1 | 8/2017 | Mishelevich |

FOREIGN PATENT DOCUMENTS

| | | |
|---|---|---|
| WO | WO-2013/102180 A1 | 7/2013 |
| WO | 2017/004562 | 1/2017 |

OTHER PUBLICATIONS

Bates, K. A., et al."Clearance mechanisms of Alzheimer's amyloid-β peptide: implications for therapeutic design and diagnostic tests." Molecular psychiatry 14.5 (2009): 469-486. (Year: 2009).*

Burgess, Alison, Isabelle Aubert, and Kullervo Hynynen. "Focused ultrasound: crossing barriers to treat Alzheimer's disease." Therapeutic delivery 2.3 (2011): 281-286. (Year: 2011).*

Scarcelli, Tiffany, et al. "Stimulation of hippocampal neurogenesis by transcranial focused ultrasound and microbubbles in adult mice." Brain stimulation 7.2 (2014): 304-307. (Year: 2014).*

EPO search report and opinion for related Application No. EP 15810036.2, 17 pages, dated Apr. 26, 2018.

Int'l Preliminary Report on Patentability for PCT/AU2015/050345, seven pages, dated Dec. 20, 2016.

International Search Report for PCT/AU2015/050345, four pages, dated Oct. 20, 2015.

Written Opinion of the ISA for PCT/AU2015/050345, five pages, dated Oct. 20, 2015.

Yoo et al. "Focused ultrasound modulates region-specific brain activity" *Neuroimage*, vol. 56, No. 3, pp. 1267-1275 (2011).

Jordão et al., "Antibodies Targeted to the Brain with Image-Guided Focused Ultrasound Reduces Amyloid-β Plaque Load in TgCRND8 Mouse Model of Alzheimer's Disease," PLoS One, 5(5): e10549 (2010) (8 pages).

* cited by examiner

NEURODEGENERATIVE DISEASE TREATMENT

CROSS REFERENCE

This application is the U. S. national phase of International Application No. PCT/AU2015/050342 filed 19 Jun. 2015, which designated the U. S. and claims priority to Australian provisional application no. 2014902366, the entire contents of each of which are hereby incorporated by reference.

FIELD OF THE INVENTION

The present invention is directed to methods for treating neurodegenerative diseases and/or improving cognitive function, in particular those associated with protein assemblies, oligomers, aggregates or deposits, using acoustic energy, such as ultrasound. An example of such a neurodegenerative disease is Alzheimer's disease.

BACKGROUND OF THE INVENTION

Various neurodegenerative diseases are associated with or caused by the aggregation and/or deposition of proteins in the brain. One such disease is Alzheimer's disease (AD) which is characterized by the presence of monomers of the Aβ peptide that first form soluble oligomers and then aggregate into extracellular fibrillar deposits known as amyloid plaques. Levels of Aβ are elevated in the AD brain because of its increased production and/or impaired removal, with recent therapeutic strategies targeting both processes. This includes the inhibition of secretases to reduce Aβ production, as well as active and, in particular, passive immunization approaches for clearance. These strategies, however, are challenging; secretase inhibition affects additional substrates with potential off-target effects, whereas passive immunization may be costly once effectiveness is demonstrated in clinical trials.

To date there are no effective treatments for improving cognitive and/or memory function in individuals having Alzheimer's disease or any other disease associated with or caused by the extracellular presence of pathogenic protein, such as protein oligomers, aggregates and/or deposits in the brain.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention addresses one or more problems outlined above.

The present invention provides a method of improving cognitive function in an individual with impaired cognitive function, the method including the steps of:
 identifying a region of the brain of the individual to be treated with acoustic energy;
 applying a clinically safe level of acoustic energy to the region, thereby saturating or substantially saturating the region with acoustic energy;
 thereby improving cognitive function in the individual.

The present invention provides a method of improving cognitive function in an individual with a neurodegenerative disease characterized by aggregation of a pathological protein, the method including the steps of:
 applying a clinically safe level of acoustic energy to sites within a region of the brain associated with the condition, thereby saturating or substantially saturating the region with acoustic energy; wherein the application to at least some of the sites does not direct the acoustic energy to imageable deposits of the protein;
 thereby improving cognitive function in the individual.

Preferably the location of imageable deposits of the protein in the brain of the individual has not been previously determined by imaging.

The present invention provides a method of improving memory in an individual with impaired memory function, the method including the steps of:
 identifying a region of the brain of the individual to be treated with acoustic energy;
 applying a clinically safe level of acoustic energy to the region, thereby saturating or substantially saturating the region with acoustic energy;
 thereby improving memory in the individual.

Preferably, identifying a region of the brain as described herein includes
 determining a volume of the brain on the basis of symptoms displayed by the individual, typically clinically observable or biochemically detectable symptoms, or
 determining a volume of the brain on the basis of a known association with a neurodegenerative disease, in particular those associated with protein oligomers, aggregates or deposits, or
 determining a volume of the brain including a volume surrounding an site having extracellular protein in a pathogenic form, such as oligomers, an aggregate or deposit.

The method of the invention further includes determining a plurality of discrete application sites for application of acoustic energy to saturate or substantially saturate the region with acoustic energy.

The method further includes determining a scanning path along which acoustic energy is to be applied to saturate or substantially saturate the region with acoustic energy. Preferably, the method further includes determining a plurality of discrete application sites for application of acoustic energy along the scanning path.

Typically, applying a clinically safe level of acoustic energy to the region includes providing acoustic energy continuously, or at application sites, along a scanning path.

In one embodiment, the scanning path is defined by a pre-determined pattern. The scanning path may be selected from the group consisting of linear, serpentine, a raster pattern, spiral and random.

Each application site may be spaced along the scanning path or each subsequent application site may overlap with the previous application site.

Applying a clinically safe level of acoustic energy to the region, includes applying acoustic energy at an application site such that a corresponding treatment volume is therapeutically affected by acoustic energy, and wherein saturating or substantially saturating the region with acoustic energy includes applying acoustic energy at a plurality of discrete application sites or one or more extended application sites such that the corresponding treatment volume(s) correspond substantially with the region.

The plurality of application sites may be selected such that treatment volumes of at least some sites overlap to form a group of treatment volumes that corresponds substantially with the region.

The plurality of application sites may be selected such that their corresponding treatment volumes overlap to form a contiguous treatment volume that corresponds substantially with the region.

The method can further include determining an order or application of acoustic energy at the plurality of application sites. The order or application of acoustic energy may be determined to apply a clinically safe level of acoustic energy. Typically this involves minimising any one or more of heating, brain swelling, red blood cell extravasation, haemorrhage or edema.

An order of application of acoustic energy to the plurality of application sites may be determined so that a minimum delay period is provided between an application of acoustic energy to application sites with adjacent or overlapping treatment volumes. Preferably, an order or application of acoustic energy does not include sequentially applying acoustic energy to application sites with adjacent or overlapping treatment volumes.

A region of the brain may the entire brain, hemisphere, forebrain or a region of the brain of the individual known to be associated with a condition involving the presence of proteins adopting pathogenic structures in an extracellular region. Such structures may be oligomers, aggregates and/or deposits. The region may be any one or more of the following cerebrum, cerebral hemisphere, telencephalon, forebrain, cortex, frontal lobe, prefrontal cortex, precentral gyrus, primary motor cortex, premotor cortex, temporal lobe, auditory cortex, inferior temporal cortex, superior temporal gyrus, fusiform gyrus, parahippocampal gyrus, entorhinal cortex, parietal lobe, somatosensory cortex, postcentral gyrus, occipital lobe, visual cortex, insular cortex, cingulate cortex, subcortical, hippocampus, dentate gyrus, cornu ammonis, amygdala, basal ganglia, striatum, caudate, putamen, nucleus accumbens, olfactory tubercle, globus pallidus, subthalamic nuclei, piriform cortex, olfactory bulb, fornix, mammillary bodies, basal forebrain, nucleus basalis Meynert, diencephalon, thalamus, hypothalamus, midbrain, tectum, tegmentum, substantia nigra, hindbrain, myelencephalon, medulla oblongata, metencephalon, pons, cerebellum, spinal cord, brain stem and cranial nerves.

In a subject identified as having Alzheimer's disease the region may be selected from the group consisting of Cerebrum, cerebral hemisphere, telencephalon, forebrain, cortex, frontal lobe, prefrontal cortex, precentral gyrus, temporal lobe, auditory cortex, inferior temporal cortex, superior temporal gyrus, fusiform gyrus, parahippocampal gyrus, entorhinal cortex, insular cortex, cingulate cortex, subcortical, hippocampus, dentate gyrus, cornu ammonis, amygdala, piriform cortex, olfactory bulb, fornix, mammillary bodies, basal forebrain and nucleus basalis Meynert. Preferably, the region is not solely identified as a plaque.

In a subject identified as having frontotemporal dementia the region may be selected from the group consisting of cerebrum, cerebral hemisphere, telencephalon, forebrain, cortex, frontal lobe, prefrontal cortex, precentral gyrus, primary motor cortex, premotor cortex, temporal lobe, auditory cortex, inferior temporal cortex, superior temporal gyrus, fusiform gyrus, parahippocampal gyrus, entorhinal cortex, parietal lobe, somatosensory cortex, postcentral gyrus, occipital lobe, visual cortex, insular cortex, cingulate cortex, subcortical, hippocampus, dentate gyrus, cornu ammonis, amygdala, basal ganglia, striatum, caudate, putamen, nucleus accumbens, olfactory tubercle, globus pallidus, subthalamic nuclei, piriform cortex, olfactory bulb, fornix, mammillary bodies, basal forebrain, nucleus basalis Meynert, midbrain, tectum, tegmentum, substantia nigra, hindbrain, myelencephalon, medulla oblongata, metencephalon, pons and cerebellum.

In a subject identified as having Parkinson's disease the region may be selected from the group consisting of substantia nigra, basal ganglia, striatum, caudate, putamen, nucleus accumbens, cerebrum, cerebral hemisphere, telencephalon, forebrain and cortex.

As used herein the acoustic energy provide may provide conditions for an increase in the permeability of the blood-brain barrier, or activating microglia. Conditions for an increase in the permeability of the blood-brain barrier are described further herein.

Preferably, a clinically safe level of acoustic energy does not result in detectable heating, brain swelling, red blood cell extravasation, haemorrhage or edema.

Acoustic energy used in the invention may be ultrasound. Ultrasound may be focused or unfocused.

An individual with impaired cognitive and/or memory function may be identified as having a neurodegenerative disease caused by the pathological aggregation of one or more of the proteins: Amyloid beta, amyloid fragments, amyloid precursor protein, amyloid precursor protein fragments and British peptide.

Typically, an improvement in cognitive function or memory is determined by standardised neuropsychological testing.

The present invention provides a method of improving memory in an individual with impaired memory function, the method including the steps of:
  providing an individual with impaired memory function;
  identifying a region of the brain of the individual to be treated with acoustic energy;
  applying a clinically safe level of acoustic energy to the region, thereby saturating or substantially saturating the region with acoustic energy;
  thereby improving memory in the individual.

The present invention provides a method of improving cognitive function in an individual with impaired cognitive function, the method including the steps of:
  providing an individual with impaired cognitive function;
  identifying a region of the brain of the individual to be treated with acoustic energy;
  applying a clinically safe level of acoustic energy to the region, thereby saturating or substantially saturating the region with acoustic energy;
  thereby improving cognitive function in the individual.

The present invention provides a method of treating a neurodegenerative disease associated with an extracellular pathogenic protein, the method including the steps of:
  providing an individual identified as having a neurodegenerative disease associated with an extracellular pathogenic protein;
  identifying a region of the brain of the individual to be treated with acoustic energy;
  applying a clinically safe level of acoustic energy to the region, thereby saturating or substantially saturating the region with acoustic energy;
  thereby treating the neurodegenerative disease in the individual.

In any aspect of the invention, the method may be conducted without the addition of an exogenous therapeutic agent.

Typically, a method of the invention also includes the step of administering an agent to promote the increase in permeability of the blood-brain barrier. In a preferred form that agent promotes cavitation. An agent that promotes cavitation may be a microbubble agent as described herein. The microbubble may be provided to the subject by continuous infusion or a single bolus. The infusion may occur sequentially to, or following the start of, or simultaneously with, the application of the ultrasound.

The present invention provides a method of treating a neurodegenerative disease associated with an extracellular pathogenic protein, the method including the steps of:

providing an individual identified as having a neurodegenerative disease associated with an extracellular pathogenic protein;

identifying a region of the brain of the individual to be treated with acoustic energy;

applying a clinically safe level of acoustic energy to the region, thereby saturating or substantially saturating the region with acoustic energy;

thereby treating the neurodegenerative disease in the individual, wherein the location of the pathogenic protein in the brain has not been previously determined in the subject. Preferably, the location of the pathogenic protein has not been determined by any imaging method such as magnetic resonance imaging (MRI).

The present invention provides a method of treating a neurodegenerative disease associated with an extracellular pathogenic protein including the steps of:

providing a subject identified as having a neurodegenerative disease associated with an extracellular pathogenic protein;

applying ultrasound to a region of the brain of the subject to increase the permeability of the blood-brain barrier, thereby treating the neurodegenerative disease.

The present invention provides a method of treating a neurodegenerative disease associated with an extracellular pathogenic protein including the steps of:

providing a subject identified has having a neurodegenerative disease associated with an extracellular pathogenic protein applying ultrasound to the entire brain or a region of the brain of the subject to increase the permeability of the blood-brain barrier;

administering a microbubble agent to the subject, thereby treating the neurodegenerative disease. Typically the step of applying the ultrasound is repeated.

Any method of the invention described herein may further include the step of determining that the permeability of the blood-brain barrier has increased.

The present invention provides a method of treating a neurodegenerative disease consisting of applying an ultrasound to the brain of a subject, thereby treating the neurodegenerative disease.

The present invention also provides a method of treating a neurodegenerative disease associated with accumulation of an extracellular pathogenic protein including positioning at least one ultrasound emitter at an anatomical location proximate to a region of the brain of a subject identified has having a neurodegenerative disease associated with an extracellular pathogenic protein;

applying ultrasound to the brain of the subject to increase the permeability of the blood-brain barrier, thereby treating the neurodegenerative disease. Typically the extracellular pathogenic protein is protein that is present exterior to the cell when the ultrasound is applied.

The present invention provides a method of improving cognitive function in an individual with a neurodegenerative disease characterized by aggregation of a pathological protein, the method including the steps of:

applying a clinically safe level of acoustic energy to sites within a region of the brain associated with the condition, thereby saturating or substantially saturating the region with acoustic energy; wherein the application to at least some of the sites does not direct the acoustic energy to imageable deposits of the protein;

thereby improving cognitive function in the individual. Preferably the location of imageable deposits of the protein in the brain of the individual has not been previously determined by imaging. The sites may be substantially uniformly distributed throughout the region or the distribution of sites throughout the region does not correlate with the distribution of imageable deposits of the protein at a statistically significant level.

The acoustic energy may be applied in a method of the invention at a pressure greater than 0.4 MPa. Typically this pressure is used when application of the acoustic energy is outside the skull, i.e. transcranially. Otherwise, the acoustic energy may be applied with a mechanical index of between 0.1 and 2.

In any method of the invention, the step of applying the acoustic energy may be repeated.

Typically, the application of the acoustic energy in a method of the invention is not image-guided.

Another embodiment of the invention is directed to an apparatus for, or when used for, increasing the permeability of the blood-brain barrier in a subject identified as having a neurodegenerative disease including: an ultrasound emitting device consisting of an ultrasound transducer with appropriate signal generation and amplification, and a fluid coupler for transmitting the ultrasonic output and a microbubble agent. The ultrasound emitting device of the apparatus may use an unfocused ultrasound transducer or an array of unfocused transducers or a phased array ultrasound transducer (i.e., focused ultrasound).

As used herein, except where the context requires otherwise, the term "comprise" and variations of the term, such as "comprising", "comprises" and "comprised", are not intended to exclude further additives, components, integers or steps. "Comprising" and "including" are intended to have the same meaning.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
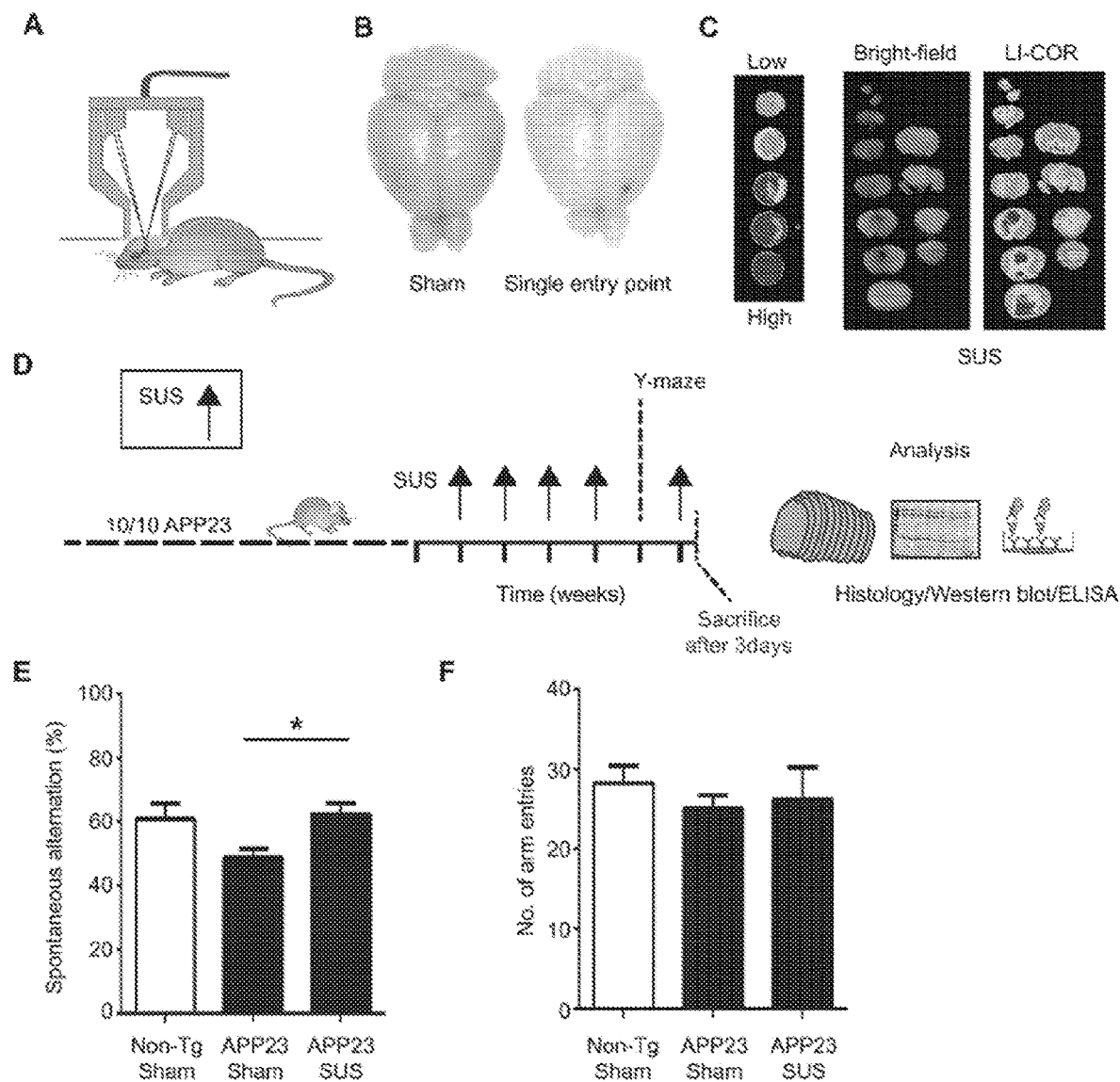
FIG. 1: Scanning ultrasound (SUS) restores memory in an Alzheimer's mouse model. (A) Setup of SUS equipment. (B and C) blood-brain barrier (BBB) opening by ultrasound was monitored by injecting wild-type mice with Evans blue dye that binds to albumin, a protein that is normally excluded from the brain. (B) A single entry point revealed a focal opening of the BBB in response to ultrasound treatment, with Evans blue dye able to enter the brain at this point. (C) Widespread opening of the BBB 1 hour after SUS was demonstrated with an Odyssey fluorescence LI-COR scanner of brain slices using nitrocellulose dotted with increasing concentrations of blue dye as a control. (D) Treatment scheme for the first cohort of hemizygous male Aβ plaque-forming APP23 mice (median age, 12.8 months). The mice received SUS or sham treatment for a total duration of the experiment of 6 weeks. Mice were randomly assigned to treatment groups. Using histological methods, Western blotting, enzyme-linked immunosorbent assay (ELISA), and confocal microscopy, we measured the effect of SUS treatment on amyloid pathology in mouse brain. Before the last SUS treatment, all mice were tested in the Y-maze. (E) The sequence of arm entries in the Y-maze was used to obtain a measure of alternation, reflecting spatial working memory. The percentage of alternation was calculated by the number of complete alternation sequences (that is, ABC, BCA, and CAB) divided by the number of alternation opportunities. Spontaneous alternation was restored in SUS-treated compared to sham-treated APP23 mice using non-Tg littermates as controls (n=10 per group; one-way ANOVA followed by Dunnett's posttest, P<0.05). (F) Total number of arm entries did not differ between groups.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All of the patents and publications referred to herein are incorporated by reference in their entirety. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

The inventors have developed a non-invasive, non-pharmacological and regionally selective therapeutic approach of restoring cognitive and/or memory function. It is believed that this is achieved by removing pathogenic protein, such as amyloid-$\beta$ ($A\beta$).

The invention is surprising as it was believed in the field that an increase in permeability of the blood-brain barrier was associated with the pathogenesis of Alzheimer's disease.

Unexpectedly, the methods of the invention do not require additional therapeutic agents, such as antibodies against $A\beta$, for treatment.

Further, the method the invention does not require identification of the location of the regions associated with pathogenic extracellular protein, for example via magnetic resonance imaging (MRI). In other words, the acoustic energy, such as ultrasound, can be directed by simple aiming techniques, such as physically orienting one or more transducers on a headpiece, thereby eliminating the complexities of electronic focusing and reduces the need for image guidance. This treatment also has the advantage of treating conditions where the precise site of therapy is not well defined. A highly focused approach is more likely to be unsuccessful or only partially cover the targeted region.

Without being bound by any theory or mode of action it is believed that increasing the permeability of the blood-brain barrier leads to at least one of the following processes: i) clearance of the pathological protein aggregates out of the brain, into the blood, following opening of the blood-brain barrier, ii) delivery of endogenous blood components such as albumin or enzymes to the brain that can bind and de-aggregate protein deposits, iii) delivery of endogenous antibodies and inflammatory molecules and complement that can reduce the protein deposits to the brain, iv) activation of microglia and astrocytes in the brain leading to phagocytosis and reduction of the protein deposits, v) entry of immune cells into brain from the blood or vasculature leading to phagocytosis and reduction of the protein deposits and/or, vi) activating processes in neuronal cells that can lead to clearance of protein deposits.

Advantages of the invention described herein include that the method is non-invasive and transcranial, does not require the administration of a therapeutic compound and does not require identification of the location of protein aggregates or deposits in the brain. The methods described herein are also advantageous as they facilitate removal of oligomeric deposits which do not exist in imageable deposits.

The blood-brain-barrier structure surrounds blood vessels in the brain and prevents most molecules in the blood from entering the brain and having effects. Conversely, the blood-brain-barrier prevents the movement or clearance of molecules in the brain from entering into the peripheral circulation. Further, invention allows a temporary increase in the permeability of the blood-brain barrier thereby allowing the natural function of the blood-brain barrier to be restored after a period of time.

A subject in need of treatment may be one that exhibits impaired memory function, cognitive function or subclinical or clinical symptoms of a neurodegenerative disease. The selection of an individual for treatment may involve a screening step for identifying whether the individual is displaying impaired cognitive function, memory function or a clinical manifestation of a neurodegenerative disease. A subject in need of treatment may be one that is identified as having early, intermediate or late stage disease and in the case of Alzheimer's disease may be identified as having either diffuse Aβ oligomers or plaques.

In Alzheimer's disease there is a significant cognitive decline from a previous level of performance in one or more areas of cognitive domains, preferably documented by standardised neuropsychological testing. The cognitive domains that are affected in Alzheimer's disease include learning and memory, complex attention, executive function, perceptual—motor, social cognition, and language. This list of domains is not exhaustive In addition, other neurodegenerative diseases that could be treated by the invention are characterised by deficits in the listed cognitive domains as well as motor function.

A decline of memory and learning is documented and at least one other cognitive domain. The decline in cognition is progressive and gradual.

Standardised neuropsychological tests of cognition that could be administered to identify an individual in need of treatment or to determine the effectiveness of the treatment include any of the following tests or one or more of its components: Neuropsychological Test Battery, Alzheimer's Disease Assessment Scale-cognitive subscale (ADAS-cog), Mini-Mental State Examination, Severe Impairment Battery, Disability Assessment Scale for Dementia, Clinical Dementia Rating Scale Sum of Boxes, Alzheimer's Disease Cooperative Study Clinical Global Impression of Change, Wechsler Memory Scale Visual Immediate, Wechsler Memory Scale Verbal Immediate, Rey Auditory Verbal Learning Test, Wechsler Memory Digit Span, Controlled Word Association Test, Category Fluency Test, Wechsler Memory Scale Visual Delayed, Wechsler Memory Scale Verbal Delayed, RAVLT delayed, Wechsler Memory Scale, Stroop Task, Wisconsin Card Sorting Task, or other tests of memory and executive function.

A patient with cognitive dysfunction caused by a neurodegenerative disease may have one or more of the following impairments in the highlighted domains, for example:
 Learning and memory: Cannot keep track of plans, repeats themselves in conversation, needs frequent reminders to perform tasks;
 Complex attention: Difficulty in environments with multiple stimuli, difficulty holding new information in mind;
 Executive function: Inability to perform complex projects, inability to make decisions;
 Language: Difficulties with expressive or receptive language, use of general terms instead of correct word, may not recall names of friends and family;
 Perceptual-motor: Difficulty with previously familiar motor tasks and activities, navigation; and
 Social cognition: Changes in behaviour, digression from social norms, makes reckless decisions, shows poor insight into these decisions.

A patient with frontotemporal dementia may show impairments in one or more of the domains of language, social cognition, perceptual-motor, executive function and complex attention without learning and memory impairment, or learning and memory impairment may be present. In Parkinson's disease motor deficits may be present with or without deficits in other domains of cognition, or deficits may be present. In Huntington's disease, motor deficits may be present without deficits in other domains of cognition, or deficits may be present. In Amyotrophic Lateral Sclerosis motor deficits may be present without deficits in other domains of cognition, or deficits may be present.

The neurodegenerative diseases to which the invention can be applied are those where pathogenic protein is extracellular and cause or contribute to the disease or a symptom thereof. The pathogenic protein may be in a pathogenic form when in an altered structure such as an oligomer, an aggregate or a deposit. Alzheimer's disease, dementia with Lewy bodies, Parkinson's disease, frontotemporal lobar degeneration and British and Danish familial dementia are non-limiting examples of diseases associated with extracellular pathogenic protein. Alzheimer's disease is the most common example of these diseases in which oligomers or plaques composed of amyloid beta are formed in the brain. Other neurodegenerative diseases are caused by the pathological aggregation of one or more of the proteins: Amyloid beta, amyloid fragments, amyloid precursor protein, amyloid precursor protein fragments or British peptide.

In a preferable embodiment the condition, disease or syndrome is Alzheimer's disease. In these embodiments the individual to be treated may display impairment in the following cognitive domains including learning and memory, complex attention, executive function, perceptual motor, social cognition, and language. Alternatively, the individual may display one or more of the following symptoms: Age-associated cognitive impairment, Age-associated neuronal dysfunction not restricted to cognitive impairment, short term memory loss, inability to acquire new information, semantic memory impairments, apathy, mild cognitive impairment, language, executive or visuoconstructional problems or apraxia, long term memory impairment, irritability and aggression, and exhaustion.

Treatment as used herein refers to therapeutic treatment and also involves ameliorating a symptom associated with a disease. Therapeutic treatment can be measured by an increase or recovery in any one or more of the group consisting of cognitive function; short term memory; ability to acquire new information; semantic memory; apathy; language, executive or visuoconstructional problems or apraxia; long term memory; irritability and aggression; or exhaustion. Treatment can also be measured via reduction in the presence of pathogenic protein or a reduction in the particular forms of pathogenic protein such as protein aggregates or deposits. The presence and reduction of the pathogenic protein that can be visualised or detected by imaging techniques or biochemical techniques described herein. For example, in relation to Alzheimer's disease, treatment may relate to a reduction in a soluble or insoluble isoforms of amyloid-β peptide or a reduction in the number of amyloid-β plaques. Alternatively, the outcome of the treatment may be determined by neuropsychological or cognitive testing. Improving memory may be determined by memory tests, typically a test administered by a clinical professional. Standardised neuropsychological tests of cognition that could be administered to test the effectiveness of the treatment include any of the following tests or one or more of its components: Neuropsychological Test Battery, Alzheimer's Disease Assessment Scale-cognitive subscale (ADAS-cog), Mini-Mental State Examination, Severe Impairment Battery, Disability Assessment Scale for Dementia, Clinical Dementia Rating Scale Sum of Boxes, Alzheimer's Disease Cooperative Study Clinical Global Impression of Change, Wechsler Memory Scale Visual Immediate, Wechsler Memory Scale Verbal Immediate, Rey Auditory Verbal Learning Test, Wechsler Memory Digit Span, Controlled Word Association Test, Category Fluency Test, Wechsler Memory Scale Visual Delayed, Wechsler Memory Scale Verbal Delayed, Rey Auditory Verbal Learning Test, Wechsler Memory Scale, Stroop Task, Wisconsin Card Sorting Task, Trail Making Test, or any other tests of memory and executive function alone or in combination.

Acoustic energy, such as ultrasound, can be applied to the entire brain or a region of the brain. A region of the brain may be a hemisphere or forebrain. The region may be at least 25% by volume of the brain. The region of the brain may be one that is known to be associated with pathogenic protein deposition. The particular regions of the brain to be targeted for effective treatment will differ depending on the disease. For example, for Alzheimer's disease the areas that may be targeted include the hippocampus, temporal lobe and/or basal forebrain, more specifically, the hippocampus, form ix, mamillary body and dentate gyrus, posterior cingulate gyrus, and temporal lobe. For Frontal Temporal Dementia the brain region to be targeted includes the cortex. For Amyotrophic Lateral Sclerosis the region to be targeted includes the spinal cord, motor cortex, brain stem.

Identifying a region of the brain to which acoustic energy is applied may include determining a volume of the brain on the basis of symptoms displayed by the individual, typically clinically observable or biochemically detectable symptoms, or determining a volume of the brain on the basis of a known association with a neurodegenerative disease, in particular those associated with protein oligomers, aggregates or deposits, or determining a volume of the brain including a volume surrounding an site having extracellular protein in a pathogenic form, such as oligomers, an aggregate or deposit.

The focus of the acoustic energy source, typically an ultrasound transducer, may be moved in a pattern with space between the individual sites of application over a region of the brain as described herein or the entire brain. The focus may be moved by a motorised positioning system.

In a preferred form, the methods of the invention involve the application of focused ultrasound to a plurality of locations in the brain. The focused ultrasound may be applied at 2, 3, 4, 5, 6, 7, 8, 9, 10 or more locations in the brain or on each hemisphere.

It is also contemplated that any disease, condition or syndrome that is a consequence of or associated with aggregation or deposition of proteins in the brain, may be treated by a method of the invention. In addition, a symptom of a disease, condition or syndrome that is a consequence of or associated with aggregation or deposition of proteins in the brain, may be reduced in severity or incidence by a method of the invention.

Increasing the permeability of the blood-brain barrier can be promoted by various agents. These agents are based on the principle that biologically inert and preformed microbubbles, with either a lipid or polymer shell, a stabilized gas core, and a diameter of less than 10 μm, can be systemically administered and subsequently exposed to non-invasively delivered focused ultrasound pulses. Microbubbles within the target volume thereby become "acoustically activated" by what is known as acoustic cavitation. In this process, the microbubbles expand and contract with the acoustic pressure rarefaction and compression over several cycles. This activity has been associated with a range of effects including the displacement of the vessel wall through dilation and contractions. It is believed that the mechanical interaction between ultrasound, microbubbles and the vasculature transiently opens tight junctions thereby increasing the permeability of the blood-brain barrier.

The microbubble agent can be any agent known in the art including lipid-type microspheres or protein-type microspheres or a combination thereof in an injectable suspension. For example, the agent can be selected from the group consisting of Octafluoropropane/Albumin (Optison), a perflutren lipid microsphere (Definity), Galactose-Palmitic Acid microbubble suspension (Levovist) Air/Albumin (Albunex and Quantison), Air/Palmitic acid (Levovist/SHU508A), Perfluoropropane/Phospholipids (MRX115, DMP115), Dodecafluoropentane/Surfactant (Echogen/QW3600), Perfluorobutane/Albumin (Perfluorocarbon exposed sonicated dextrose albumin), Perfluorocarbon/Surfactant (QW7437), Perfluorohexane/Surfactant (Imagent/AF0150), Sulphur hexafluoride/Phospholipids (Sonovue/BR1), Perfluorobutane/Phospholipids (BR14), Air/Cyanoacrylate (Sonavist/SHU563A), and Perfluorocarbon/Surfactant (Sonazoid/NC100100).

The microbubble agent may be provided as a continuous infusion or as a single bolus dose. A continuous infusion of microbubble, preferably provided over the duration of the ultrasound application, would be preferred. Typically, the microbubble agent is delivered intravenously through the systemic circulation.

For methods of the invention that include the use of an agent such as a microbubble or other cavitation based promotion of blood-brain barrier permeability, the agent may be localized at, or near, or in a region that is targeted with the ultrasound such that the potential of unwanted damage from cavitation effects is minimised.

The applying step, for the delivery of ultrasound, may comprise the delivery of ultrasound from an ultrasound source through a fluid coupler applied directly to the head of the subject. In this application, the fluid coupler may be applied to only one side or aspect of the subject's head. The head may be an unmodified head or a head with a surgically created window in the skull—the fluid coupler being in contact with the window. The ultrasound may be generated by an unfocused ultrasound transducer or a phased array ultrasound transducer (i.e., focused ultrasound). Significantly, the phased array ultrasound transducer may be a diagnostic phased array. Diagnostic phased arrays are generally of lower power and are commonly available. The fluid coupler may comprise a contained volume of fluid (e.g., about 50 cc, about 100 cc, about 200 cc, about 400 cc, about 500 cc, about 600 cc or about 1 litre). The fluid may be, for example, water, ultrasonic gel, or a substance of comparable acoustic impedance. The fluid may be contained in a fluid cylinder with at least a flexible end portion that conforms to the subject's head. In other embodiments, the contained volume of fluid may be a flexible or elastic fluid container.

Increased permeability of the blood-brain barrier may be determined by any suitable imaging method. Preferably, the imaging method is MRI, an optical imaging method, positron emission tomography (PET), computerized tomography (CT) or computerized axial tomography (CAT) or ultrasound. If a level of acoustic energy is applied, the increased permeability of the blood-brain barrier could then be determined by any one of the methods described herein and an increased level of acoustic energy could be subsequently applied until the permeability of the blood-brain barrier had increased to a clinically relevant level.

Any ultrasound parameters that result in clinically safe application of acoustic energy are useful in the invention. Typically, the ultrasound parameters that are preferred as those that result in an increase the permeability of the blood-brain barrier, or activate microglia phagocytosis. Various ultrasound parameters can be manipulated to influence the permeability increase in the blood-brain barrier and these include pressure amplitude, ultrasound frequency, burst length, pulse repetition frequency, focal spot size and focal depth. Several parameters are now described that are useful in a method of the invention.

Focal spot size useful in a method of the invention includes about a 1 mm to 2 cm axial width. Typically, the focal spot size has an axial width of about 1 mm to 1.5 cm, preferably 1 mm to 1 cm, even more preferably 1 mm to 0.5 cm. The length of the focal spot may be about 1 cm to as much as about 15 cm, preferably 1 cm to 10 cm, even ore preferably 1 cm to 5 cm. The focal size useful in a method of the invention is one that allows an increase in the permeability of the blood-brain barrier of the subject.

The focal depth of the ultrasound generally depends on the areas of the brain affected by the disease. Therefore, the maximum focal depth would be the measurement from the top of the brain to the base, or about 10 to about 20 cm. Focal depth could be altered by electronic focusing, preferably by using an annular array transducer.

Typically the ultrasound is applied in continuous wave, burst mode, or pulsed ultrasound. Preferably the ultrasound is applied in burst mode, or pulsed ultrasound. Pulse length parameters that are useful in a method the invention include between about 1 to about 100 milliseconds, preferably the pulse length or burst length is about 1 to about 20 milliseconds. Exemplary burst mode repetition frequencies can be between about 10 Hz to 100 kHz, 10 Hz to 1 kHz, 10 Hz to 500 Hz or 10 Hz to 100 Hz.

The duty cycle (% time the ultrasound is applied over the time) is given by the equation duty cycle=pulse length×pulse repetition frequency×100. Typically, the duty cycle is from about 0.1% to about 50%, about 1% to about 20%, about 1% to about 10%, or about 1% to about 5%.

The ultrasound pressure useful in a method of the invention is the minimum required to increase the permeability of the blood-brain barrier. The human skull attenuates the pressure waves of the ultrasound which also depends on the centre frequency of the transducer, with lower centre frequencies of the ultrasound transducer causing better propagation and less attenuation. A non-limiting example of ultrasound pressure is between 0.1 MPa to 2 MPa, preferably about 0.4 or 0.5 MPa. Typically this pressure is applied to the skull, i.e. transcranially. The mechanical index characterises the relationship between peak negative pressure amplitude in situ and centre frequency with mechanical index=Pressure (MPa)/sqrt centre frequency (MHz) if this mechanical index was free from attenuation/measured from within the skull, the mechanical index would be between about 0.1 and about 2, preferably about 0.1 to 1 or 0.1 to 0.5.

A non-limiting example of a system that is able to open the blood-brain barrier is the TIPS system (Philips Research). It consists of a focused ultrasound transducer that generates a focused ultrasound beam with a centre frequency of 1-1.7 MHz focal depth of 80 mm, active outer diameter 80 mm, active inner diameter 33.5 mm which is driven by a programmable acoustic signal source within the console and attached to a precision motion assembly. An additional example of a system that is able to generate an ultrasound beam suitable for blood-brain barrier disruption is the ExAblate Neuro (Insightec) system. Suitable parameters for blood-brain barrier opening in humans such as centre frequency and microbubble dosage may be different to that in mice.

For any of the method or apparatus of the invention, the ultrasound transducer may have an output frequency of between 0.1 to 10 MHz, or 0.1 to 2 MHz. The ultrasound may be applied for a time between 10 milliseconds to 10 minutes. The ultrasound may be applied continuously or in a burst mode.

Image contrast agents, used in any methods of the invention, may be selected from the group consisting magnetic resonance contrast agents, x-ray contrast agents (and x-ray computed tomography), optical contrast agents, positron emission tomography (PET) contrast agents, single photon emission computer tomography (SPECT) contrast agents, or molecular imaging agents. For example, the imaging contrast agent may be selected from the group consisting of gadopentetate dimeglumine, Gadodiamide, Gadoteridol, gadobenate dimeglumine, gadoversetamide, iopromide, Iopamidol, Ioversol, or Iodixanol, and Iobitridol.

The frequency of application of the ultrasound would generally depend on patient severity. The parameters of the ultrasound and the treatment repetition are such that there is an increase in permeability of the blood-brain barrier but preferably wherein there is no, or clinically acceptable levels of, damage to parenchymal cells such as endothelial or neuronal damage, red blood cell extravasation, haemorrhage, heating and/or brain swelling.

Any method of the invention may further include performing magnetic resonance imaging on a subject comprising the steps of (a) administering a magnetic resonance contrast agent to a subject through the blood-brain barrier using any of the methods of the invention and performing magnetic resonance imaging on said subject. In this context the use of magnetic resonance imaging is to confirm the increase in permeability of the blood-brain barrier and not to locate the presence of a pathogenic protein.

Another embodiment of the invention involves providing an imaging contrast agent to the whole brain including the steps of administering an imaging contrast agent into the bloodstream of said subject; and applying ultrasound to the brain of said subject to open the blood-brain barrier to allow the image contrast agent to cross the blood-brain barrier. The imaging contrast agent can be administered to the subject simultaneously or sequentially with the application of the ultrasound. In this embodiment the sequential administration of the contrast agent can be prior to or post application of the ultrasound. In a preferred embodiment, any of the agents described herein may be administered to the bloodstream between 1 to 4 hours, between 2 to 4 hours or between 3-4 hours after ultrasound treatment using one of the methods of the invention.

The examples that follow are intended to illustrate but in no way limit the present invention.

EXAMPLES

This aim of this study was to establish whether a transient opening of the BBB by 'scanning' the brain with an ultrasound focus could assist in Aβ clearance.

Here is presented a non-invasive and nonpharmacological therapeutic approach of removing Aβ and fully restoring memory functions in Aβ-depositing mice, by repeated scanning ultrasound (SUS) treatments of the brain.

Experimental data has been generated by weekly scanning ultrasound (SUS) treatments of the brain in a 12-13 month-old Aβ-depositing APP23 mouse model. The researchers have found that SUS combined with intravenously injected microbubbles temporarily disrupts the blood-brain barrier (BBB) without causing tissue damage. Importantly, SUS in combination with microbubbles achieved a full restoration of spatial memory in the Ymaze, spatial memory and learning in the APA test, short term memory, recognition and visual memory in the NOR test, as well as a reduction of plaques and Aβ levels with an efficacy comparable to that of passive Aβ immunisation.

Example 1

Figure 9:
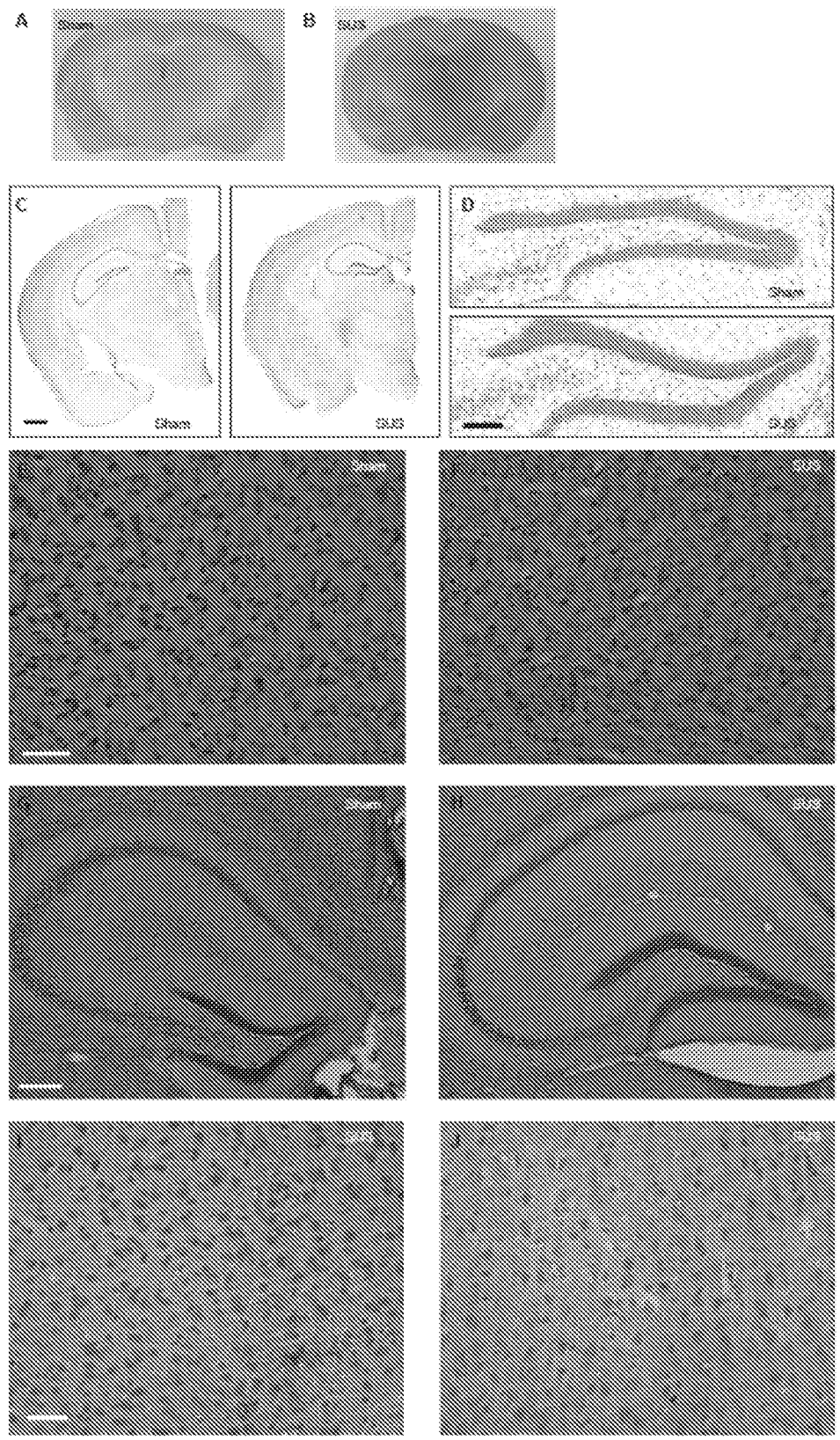
FIG. 9. Absence of brain damage after either repeated or short term scanning ultrasound (SUS) treatment. (A,B) The BBB is opened throughout the brain after SUS treatment, as evidenced by prevalent Evans Blue extravasation as early as 30 min after the treatment. (C-E) Absence of edemas, erythrocyte extravasation and 'dark' neurons revealed by Nissl staining (close-up: dentate gyrus) of cohort 1 (APP23 mice, 5 treatments over a period of six weeks) (C-D) and (E-H) hematoxylin and eosin staining, showing the cortex (E,F), and the hippocampus (G,H). (I,K) Absence of ischemic damage after SUS treatment of wild-type mice either 4 h (I) or 24 h after SUS treatment (J) using acid fuchsin staining. Scale bars: C=1 mm, E,F=50 µm, D,G,H=200 µm, I,K=50 µm.

It was first established in C57BL/6 wild-type mice that the BBB can be opened repeatedly by ultrasound, without causing tissue damage, either by using single entry points or by scanning ultrasound (SUSing) the entire brain (FIGS. 1 and 9). Mice were anaesthetized, injected intravenously with microbubbles together with Evans Blue (EB) in pilot experiments to demonstrate successful BBB opening, and placed under the focus of a TIPS ultrasound transducer (Philips), with ultrasound gel being applied to the head (FIG. 1A). Brain dissection revealed that a single pulse resulted in a 1 mm wide blue column demonstrating focused opening of the BBB (FIG. 1B). When the focus of the ultrasound beam was moved in 1.5 mm increments until the entire forebrain of the mouse was sonicated (SUSed), the BBB was opened throughout the brain, as evidenced by prevalent EB extravasation as early as 30 min after the treatment (FIG. 1B and FIGS. 9A and B). We optimized the ultrasound settings and established that 0.8 MPa peak rarefactional pressure, 10 Hz pulse repetition frequency, a 10% duty cycle, and 6 sec sonication time per spot caused neither edemas nor erythrocyte extravasation as shown by hematoxylin and eosin staining, nor 'dark' neurons as revealed by Nissl staining (FIG. 9).

We next SUSed ten 12-13 month-old male Aβ plaque-forming APP23 mice over a period of six weeks (FIG. 1D). At this age, APP23 mice have a substantial plaque burden and spatial memory deficits (L. M. Ittner et al., Cell 142, 387 (2010)). APP23 mice in the control group (n=10) received all injections and were placed under the ultrasound transducer, but no ultrasound was emitted. After the four-week treatment period the mice underwent behavioural testing in a two-week period in which they were not treated. We analyzed spatial memory functions in the Y-maze. This revealed that spontaneous alternation in the SUSed APP23 mice, but not the sham-treated animals, was restored to wild-type levels (one-way ANOVA, followed by Dunnett's multiple comparison, $P<0.05$) (FIG. 1E). Total arm entries did not differ between groups (FIG. 1F).

Figure 2:
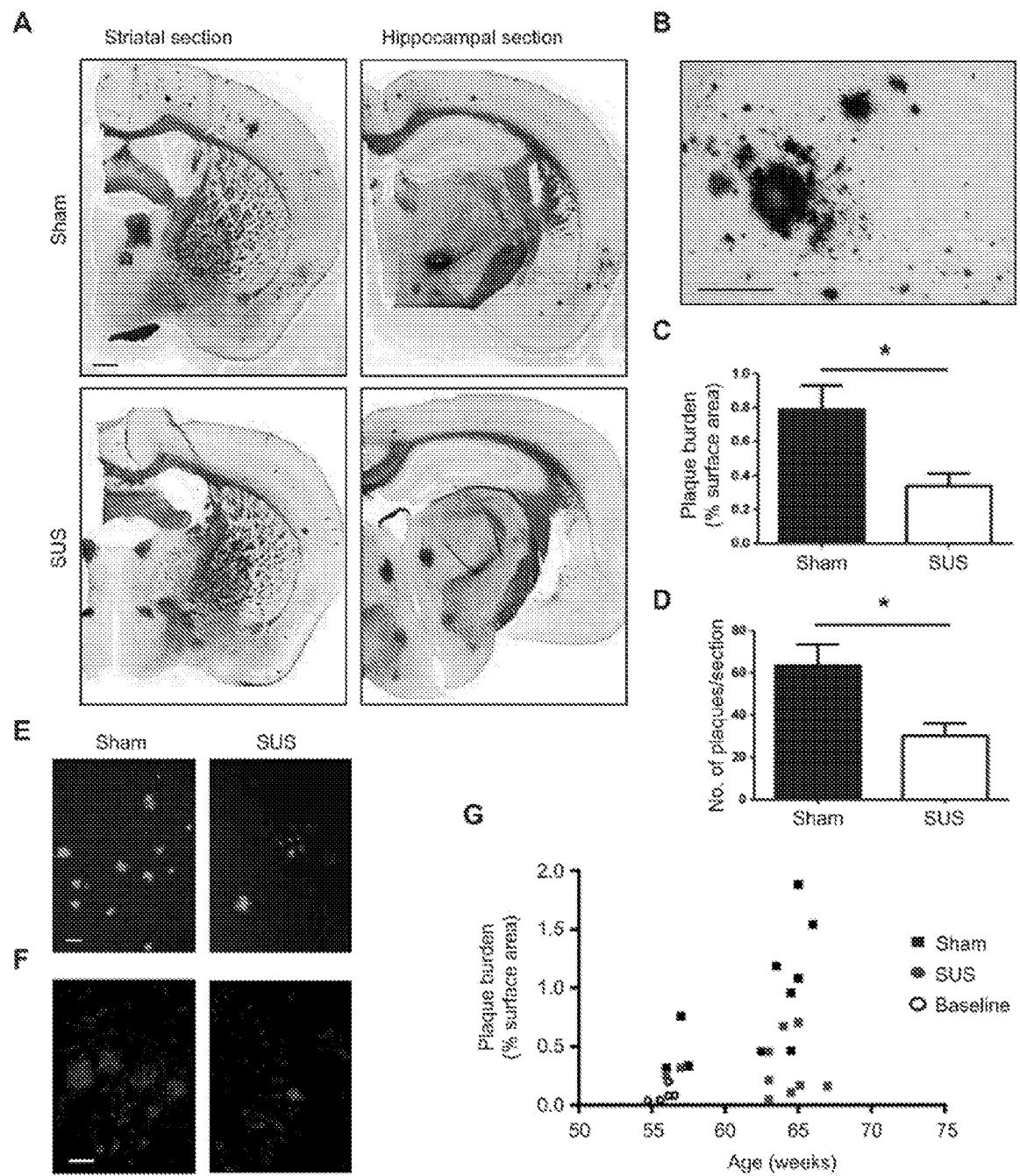
FIG. 2: SUSing reduces Aβ plaques in an Alzheimer's mouse model. (A) Representative images of free-floating coronal sections from 12 month-old APP23 mice with and without treatment. Campbell Switzer silver staining reveals compact, mature plaques (amber) and more diffuse Aβ deposits (black), see close-up (B). (C,D) Quantification of amyloid plaques reveals a 56% reduction in the area of cortex occupied by plaques (unpaired t-test, P=0.017) and a 52% reduction in plaque number per section (t-test, P=0.014) in SUSed compared to sham-treated APP23 mice (n=10 per group). Representative sections of SUSed versus control brains stained with Thioflavin S (E) and 4G8 (F). Scale bars: A=1 mm, B,F,G=200 μm. (G) Plaque load plotted as a function of age confirmed that the SUS-treated group had significantly lower plaque load than the sham-treated group. Baseline plaque load at the onset of treatment is indicated by open circles. Scale bars, 1 mm (panel A) and 200 μm (panel B).

The mice received one additional ultrasound treatment and were sacrificed four days later for histological and biochemical analysis. We first used Campbell-Switzer silver staining that can distinguish the compact core of mature plaques from more dispersed Aβ deposits (FIG. 2A,B). By analyzing every 8th section from −0.8 to −2.8 mm from bregma for each mouse (total of 8-10 sections per mouse), we found that the percentage area of the cortex occupied by plaques was reduced by 56% (unpaired ttest, P=0.014) (FIG. 2C) and the average number of plaques per section was reduced by 52% (unpaired t-test, P=0.017) (FIG. 2D) in the SUSed compared to sham-treated mice. Thioflavin S (FIG. 2E) and immunohistochemistry with the Aβ-specific antibody 4G8 (FIG. 2F) was used to confirm the specificity of the silver staining. We also plotted plaque load, as determined in FIG. 2C, as a function of age and included untreated mice to demonstrate the baseline of plaque load at the onset of treatment (FIG. 2G).

Figure 3:
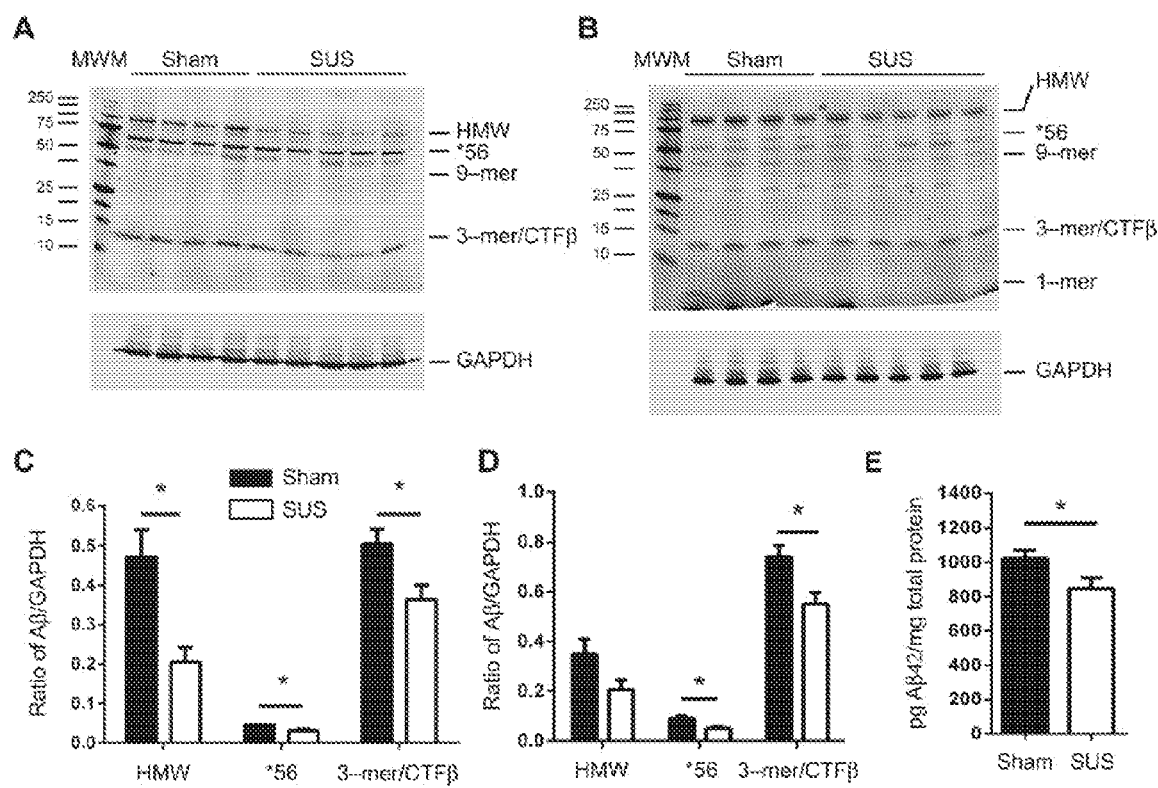
FIG. 3: SUSing reduces Aβ and APP fragments in Alzheimer's mouse model. (A to D) Western blotting of extracellular-enriched (A) and Triton-soluble (B) fractions of the brains of the first cohort of APP23 mice with 6E10 and 4G8 anti-Aβ antibodies revealed a reduction in distinct Aβ species in both fractions in SUS-treated compared to sham-treated mice. These data are quantified in (C) and (D), respectively. The Western blots show significant reductions of HMW species (incl. sAPP and Aβ), the 56-kD oligomeric Aβ*56 (*56) and trimeric Aβ (3-mer)/CTFβ, in the extracellular-enriched fraction and of *56 and 3-mer/CTFβ in the Triton-soluble fraction (unpaired t tests, P<0.05). GAPDH (glyceraldehyde 3-phosphate dehydrogenase) was used for normalization. MWM, molecular weight marker. (E) ELISA for Aβ42 in the Triton-soluble fraction revealed a significant reduction in SUS-treated compared to sham-treated mouse brains (unpaired t test, P<0.05; n=10 per group).
Figure 4:
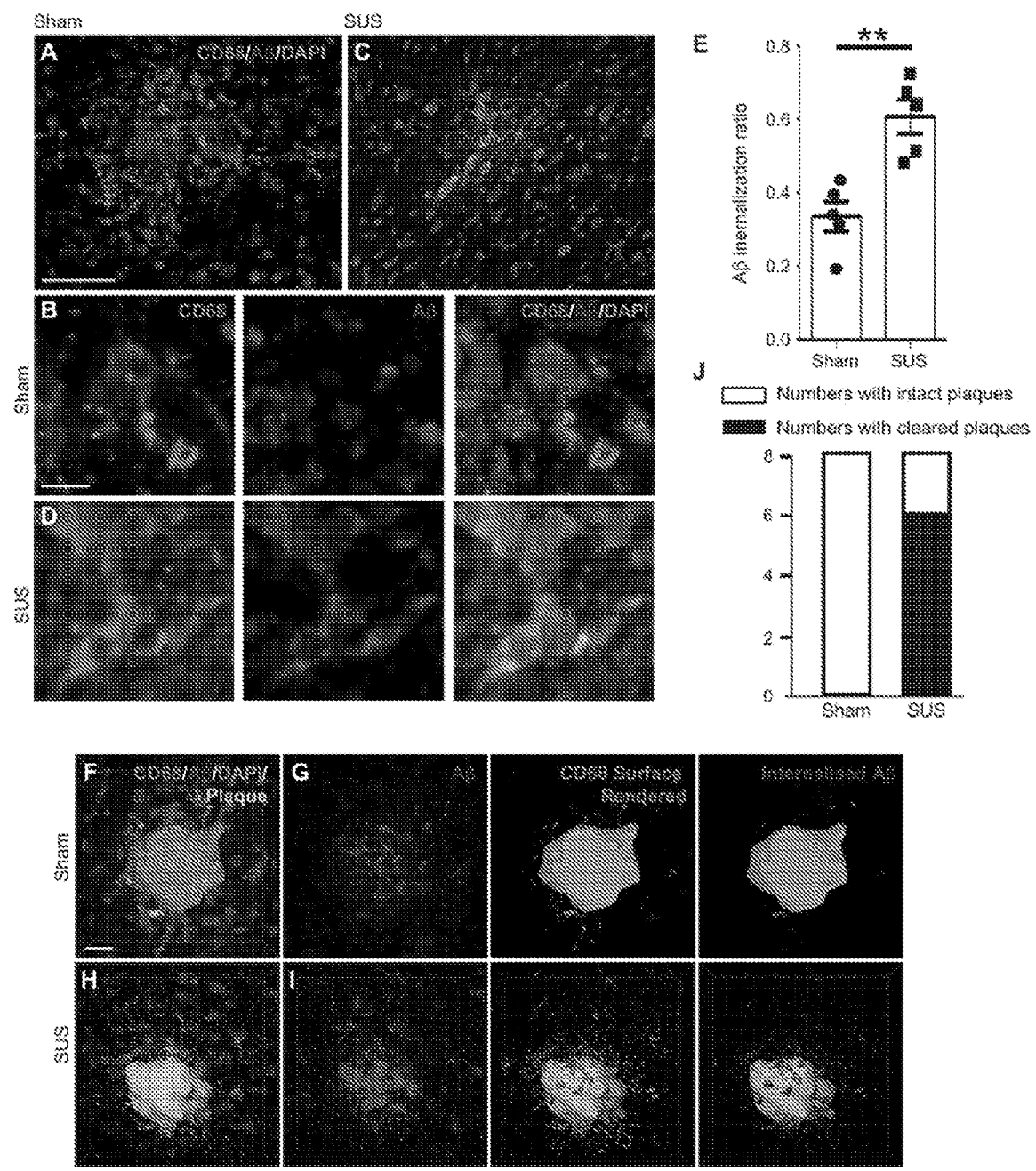
FIG. 4: Microglial phagocytosis and lysosomal uptake of Aβ induced by SUS treatment. (A and B) Plaques in sham-treated animals were surrounded by lysosomal CD68-positive microglia that contained some Aβ. (C and D) In contrast, plaques in SUS-treated mouse brains were surrounded by microglia that contained significantly more Aβ in their lysosomal compartments, with some plaques appearing to be completely phagocytosed by microglia. (E) A twofold increase in microglia-internalized Aβ was observed in SUS-treated compared to sham-treated mouse brains (unpaired t test, P=0.002). (F to I) Plaques imaged at high magnification in 3D. CD68 labeling revealed the extent of Ara at the plaque site that was internalized by microglia into lysosomes. 4',6-Diamidino-2-phenylindole (DAPI) was used to visualize nuclei. (J) Confocal analysis of Aβ and CD68 revealed that 6 of 8 SUS-treated mice and 0 of 8 sham-treated mice had "cleared plaques" in cortical areas, with Aβ being almost completely within microglial lysosomes (Fisher's exact test, P=0.007; n=8 per group, with four sections analyzed in each case). Scale bars, 100 μm (A and C) and 10 μm (B, D, and F to I).

We then extracted the right hemisphere from 10 SUSed and 10 sham-treated APP23 mice and used these to obtain two lysates, one fraction enriched in extracellular proteins and a Triton-soluble fraction (S. Lesne et al., Nature 440, 352 (2006)). By Western blotting with antibodies against Aβ we were able to identify different species (FIG. 3A,B). Levels of the Aβ species were quantified and significant reductions were found in the extracellular fraction for SUSed compared to sham-treated mice for high molecular weight species including soluble APP (HMW incl. sAPPα; 58% reduction), *56 oligomeric Aβ (Aβ*56; 38% reduction) and the trimeric Aβ/toxic APP carboxy-terminal fragment (CTFβ; 29% reduction) (FIG. 3C), and for *56 (50%) and trimeric Aβ/CTFβ (27%) in the Triton-soluble fraction (unpaired t-tests, P<0.05) (FIG. 3D). By ELISA a 17% reduction was revealed for Aβ42 in SUSed compared to sham-treated mice (unpaired t-test, P<0.05, n=10 per group) (FIG. 3E).

The degree of Aβ reduction achieved by SUSing is comparable to that achieved by passive Aβ immunization (A. Wang, P. Das, R. C. Switzer, 3rd, T. E. Golde, J. L. Jankowsky, J Neurosci 31, 4124 (2011); J. L. Frost et al., Neurodegener Dis 10, 265 (2012)), but remarkably SUSing works without an additional therapeutic agent such as antibodies against Aβ. For passive vaccinations, a range of mechanisms have been proposed to remove Aβ from the brain, with variable effects on microglial activation. Blood-borne immune molecules including Aβ-specific antibodies have been shown to assist in the phagocytosis of Aβ by microglia and perivascular macrophages. Albumin is another Aβ-neutralizing molecule that is present in the blood and may establish a 'peripheral sink'. The fact that Evans Blue-bound albumin can be detected in the brain after SUSing suggests that it may assist in the engulfment of Aβ not only in the periphery but also in the brain (FIG. 1A). It has been shown that albumin enters the brain following disruption of the BBB by ultrasound and is rapidly phagocytosed by glial cells but not neurons. Albumin has also been demonstrated to bind to Aβ and inhibit the aggregation of the peptide. We propose that following SUS treatment, albumin enters the brain and binds Aβ and the complex is then phagocytosed by microglia, explaining the ability of SUS to increase phagocytosis of Aβ, as well as to reduce the levels of Aβ oligomers.

To analyze microglial activation we used spinning disk confocal microscopy, which revealed that microglia in SUSed brains engulf plaques and that they contain twofold (unpaired t-test, P=0.002) more Aβ in lysosomal compartments than in the sham treated APP23 mice, as shown by co-staining for Aβ and the microglial lysosomal marker CD68 (FIG. 4A-D,E). High-resolution 3D-reconstruction revealed extensive Aβ internalization in SUSed compared with sham-treated brains (FIG. 4F to I). Confocal analysis of Aβ and CD68 further revealed 'cleared plaques' in cortical areas in SUS-treated mice for which Aβ was almost completely within microglial lysosomes. These were observed in 75% of the SUSed mice and never in the sham-treated mice (Fisher's exact test, p=0.007, eight mice per group, with four sections analyzed in each case (FIG. 4J). Together our results reveal that SUSing engages resident microglia and promotes internalization of Aβ, although additional studies are needed to determine the relative role of the different endogenous mechanisms that are likely to remove A. To avoid a potentially excessive immune activation in a clinical setting (K. M. Lucin, T. Wyss-Coray, Neuron 64, 110 (2009)), the ultrasound treatment regimen might be done step-wise covering one brain area at a time.

Spinning disk confocal microscopy and high resolution 3D-reconstruction reveal extensive internalization of Aβ in microglia in SUSed compared with sham-treated brains. Cleared plaques were observed in 75% of the SUSed mice but never in the sham-treated animals. Given that repeated SUSing does not cause brain damage, our study highlights its potential as a viable therapeutic approach for AD.

Figure 5:
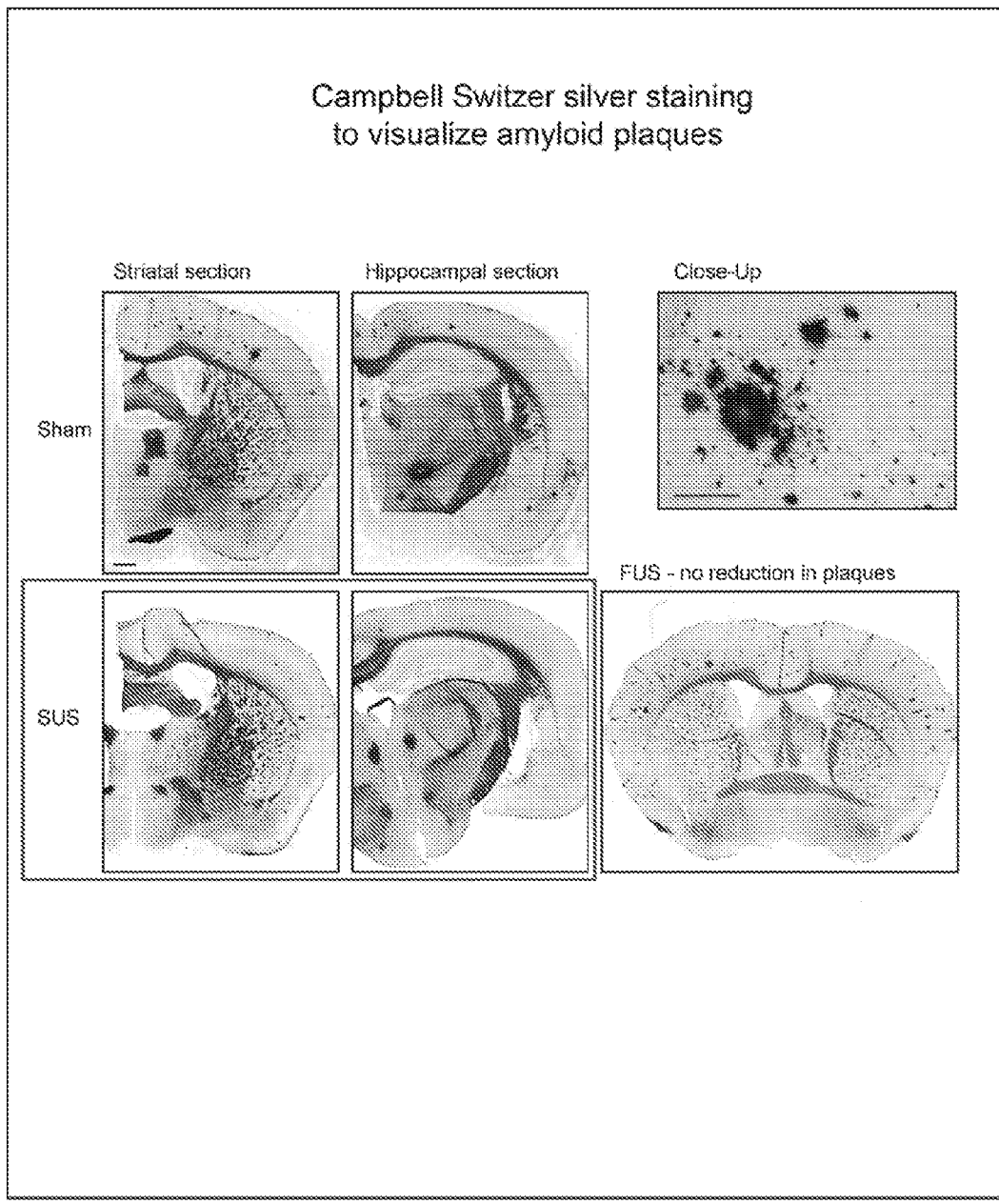
FIG. 5: Brains taken from age-matched APP23 mice where only single entry points were used once; this did not result in significant reductions in Aβ pathology.

Brains taken from age-matched APP23 mice where ultrasound was applied at only single entry points did not result in significant reductions in Aβ pathology (see, FIG. 5). This highlights the advantage of multiple ultrasound application sites as described herein.

Figure 6:
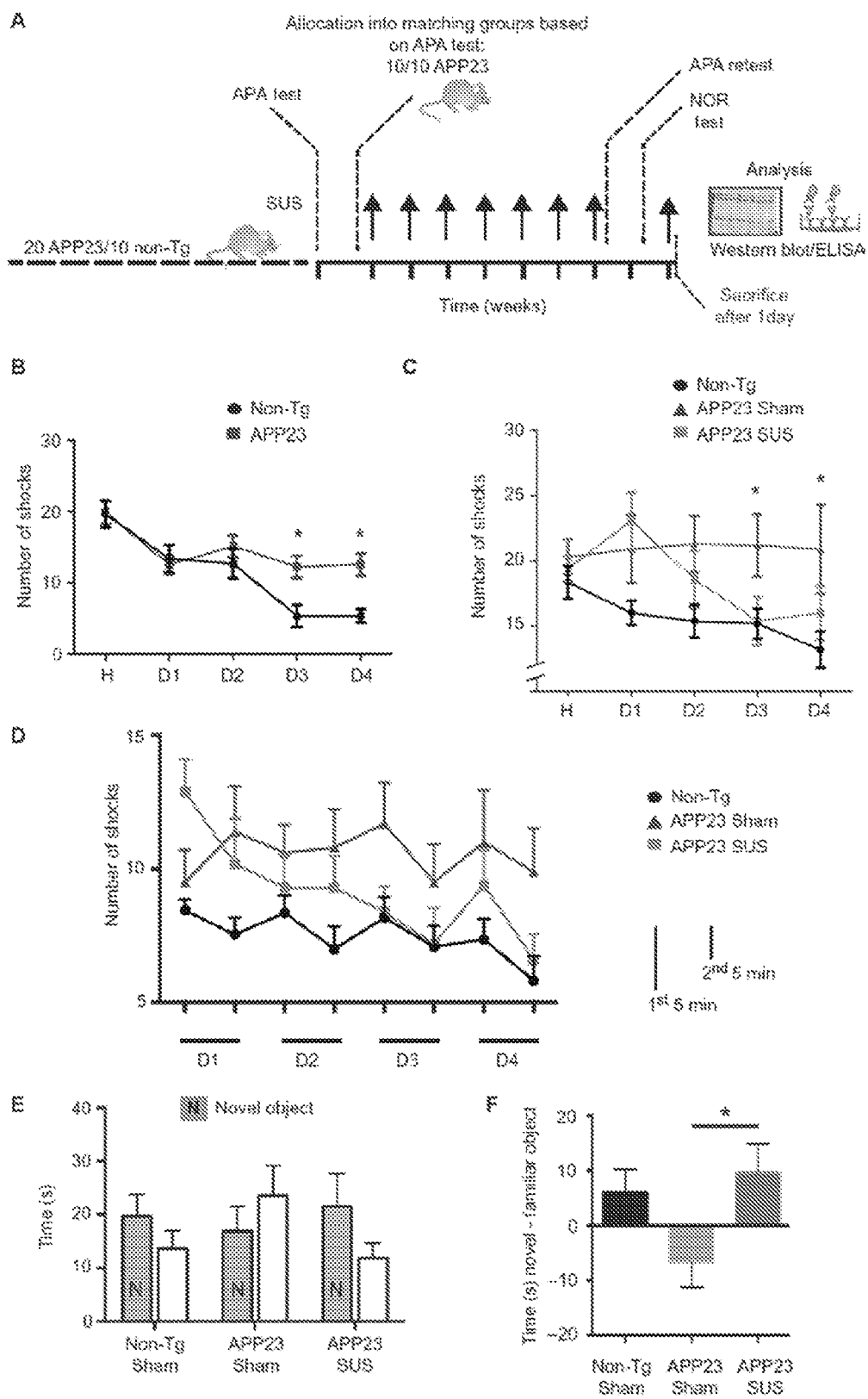
FIG. 6. SUS treatment rescues memory deficits in an AD mouse model. (A) Treatment scheme of a second cohort of 20 gender-matched APP23 mice and 10 non-Tg littermates to determine the functional outcome of the SUS treatment protocol in more robust behavioral tests. The mice were analyzed in the APA task, a test of hippocampus dependent spatial learning in which mice learned to avoid a shock zone in a rotating arena. After the APA test, the APP23 mice were divided into two groups with matching performance and received weekly SUS or sham treatment for 7 weeks. This was followed by an APA retest and a novel object recognition (NOR) test. One day after the final SUS treatment, mice were sacrificed and brain extracts were analyzed by Western blotting and ELISA. (B) Twenty APP23 mice and 10 non-Tg littermates tested in the APA test, with a habituation session (labeled H) followed by four training sessions (labeled D1 to D4). (C) In the APA retest, SUS-treated mice showed better learning than did sham treated mice when tested for reversal learning (P=0.031). (D) SUS-treated mice also showed improvement when the first 5 min (long-term memory) and last 5 min (short-term memory) were plotted separately (P=0.031). (E) The APA retest was followed by the NOR test to determine the time spent with the novel object (labeled N) compared with the familiar object. (F) Analysis of the discrimination ratio that divides the above measure by the total time spent exploring both objects revealed that SUS-treated APP23 mice showed an increased preference for the novel object compared to sham-treated APP23 mice (P=0.036).

To determine the functional outcome of our SUS treatment protocol in more robust behavioral tests, we next analysed a second cohort of 20 gender-matched APP23 mice and non-Tg littermates (n=10) in the active place avoidance (APA) task, a test of hippocampus-dependent spatial learning in which mice learn to avoid a shock zone in a rotating arena (FIG. 6A, study design). APP23 mice and non-Tg littermates underwent 4 days of training after habituation. There were significant effects of day of training ($F_{3,84}$=5.49, P=0.002) and genotype ($F_{1,28}$=5.41, P=0.028, two-way ANOVA), with day as the within-subjects factor (FIG. 6B). APP23 mice were divided into two groups with matching performance on the APA test and received weekly SUS or sham treatment for 7 weeks. Mice were retested in the APA test with the location of the shock zone in the opposite area of the arena (reversal learning). In the retest, there was a significant effect of day ($F_{3,84}$=2.809, P=0.044) and treatment group ($F_{2,28}$=3.933, P=0.0312). Multiple comparisons test for simple effects within rows showed that SUS-treated mice received fewer shocks on days 3 (P=0.012) and 4 (P=0.033) (FIG. 6C). SUS-treated mice also showed improvement when the first 5 min (long-term memory) and the last 5 min (short-term memory) of their performance were plotted separately ($F_{2,28}$=3.951, P=0.0308) (FIG. 6D). We also performed an NOR test, which revealed improved performance after SUS treatment, with SUS-treated mice showing a preference for the novel object (labeled N, FIGS. 6, E and F) [$F_{2,28}$=2.99, P=0.066; t(20)=2.33, P=0.0356] compared to sham-treated control animals.

Figure 11:
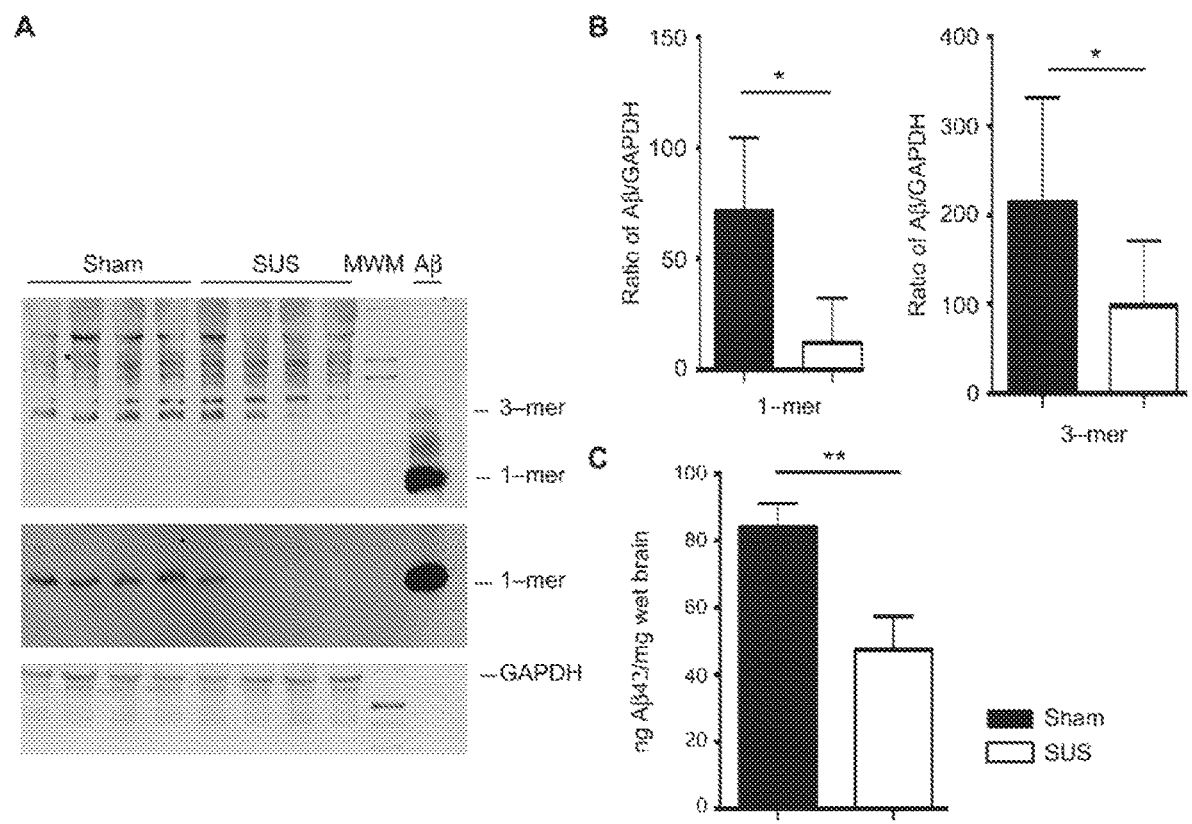
FIG. 11. SUS treatment reduces $A\beta$ in a second cohort of AD mice. (A) A second cohort of APP23 mice was analyzed by Western blot with the anti-$A\beta$ antibody W0-2; gel and transfer conditions were optimized to reveal the monomer and trimer specifically. The monomer was efficiently captured by using two sandwiched membranes. (B) The blots showed significant reduction of the monomer (fivefold reduction) and trimer (twofold reduction) in the extracellular fraction (unpaired t tests, $P<0.05$). (C) ELISA for $A\beta 42$ in the guanidine-insoluble fraction revealed a twofold reduction in SUS-treated compared to sham-treated mice (unpaired t test, $P<0.008$; n=10 per group).

Upon sacrifice, we conducted a Western blot analysis using the Aβ specific antibody W0-2, which showed a fivefold reduction of the monomer and a twofold reduction of the trimer in SUS-treated compared to sham-treated APP23 mice (unpaired t tests, P<0.05) (FIGS. 11, A and B). ELISA of the guanidine-insoluble brain fraction revealed a twofold reduction inAb42 in SUS-treated samples (P<0.008, unpaired t test) (FIG. 11C). Together, these data demonstrate that SUS has a robust effect on Aβ and memory function in AD mice.

Figure 7:
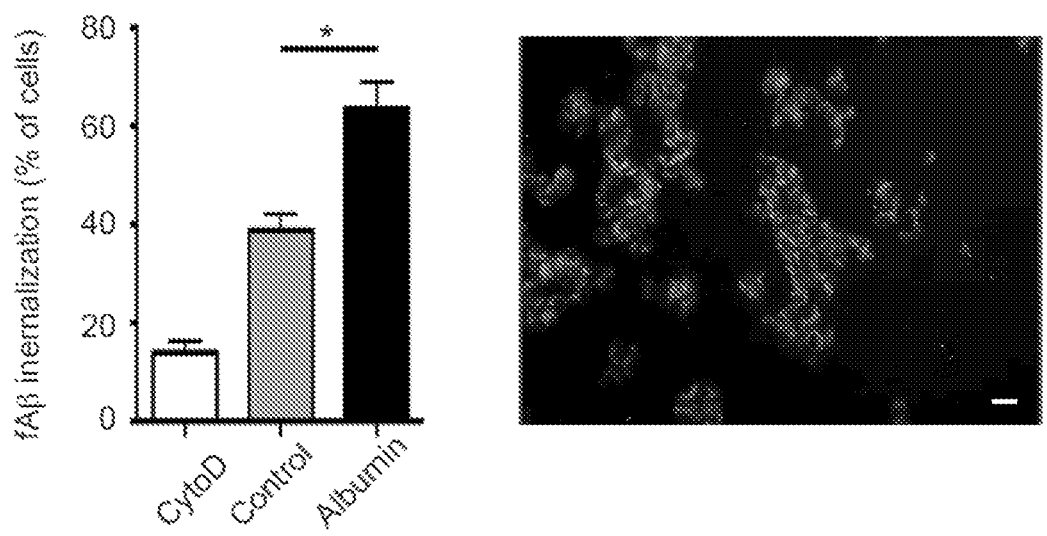
FIG. 7. Increased Aβ uptake by microglial cells in the presence of albumin. Aβ$_{42}$ uptake increases by 65% by the presence of albumin in BV-2 microglial cells (t-test, P=0.0188). Cytochalasin D was included as control to inhibit uptake. A BV-2 culture co-incubated with albumin is shown (green: LAMP2; red: Aβ). Scale bar: 25 μm.

Phagocytosis of Aβ by microglia and perivascular macrophages has been shown to be assisted by blood-borne immune molecules, including Aβ-specific antibodies. Another Aβ-neutralizing molecule is albumin, which is present in the blood and may establish a "peripheral sink". The fact that Evans blue dye-bound albumin can be detected in the brain after SUS treatment suggested that albumin may assist in Aβ engulfment not only in the periphery but also in the brain. To determine whether albumin may facilitate Aβ uptake by microglia, we incubated microglial BV-2 cells in culture with Aβ42 with and without albumin (10 mg/ml; equivalent to 20% of the concentration in human serum) and found a 65% increase in Aβ42 uptake in the presence of albumin (t test, P=0.0188) (FIG. 7). This result suggested that after SUS treatment, albumin may enter the brain and bind to Aβ, facilitating microglial phagocytosis.

Figure 8:
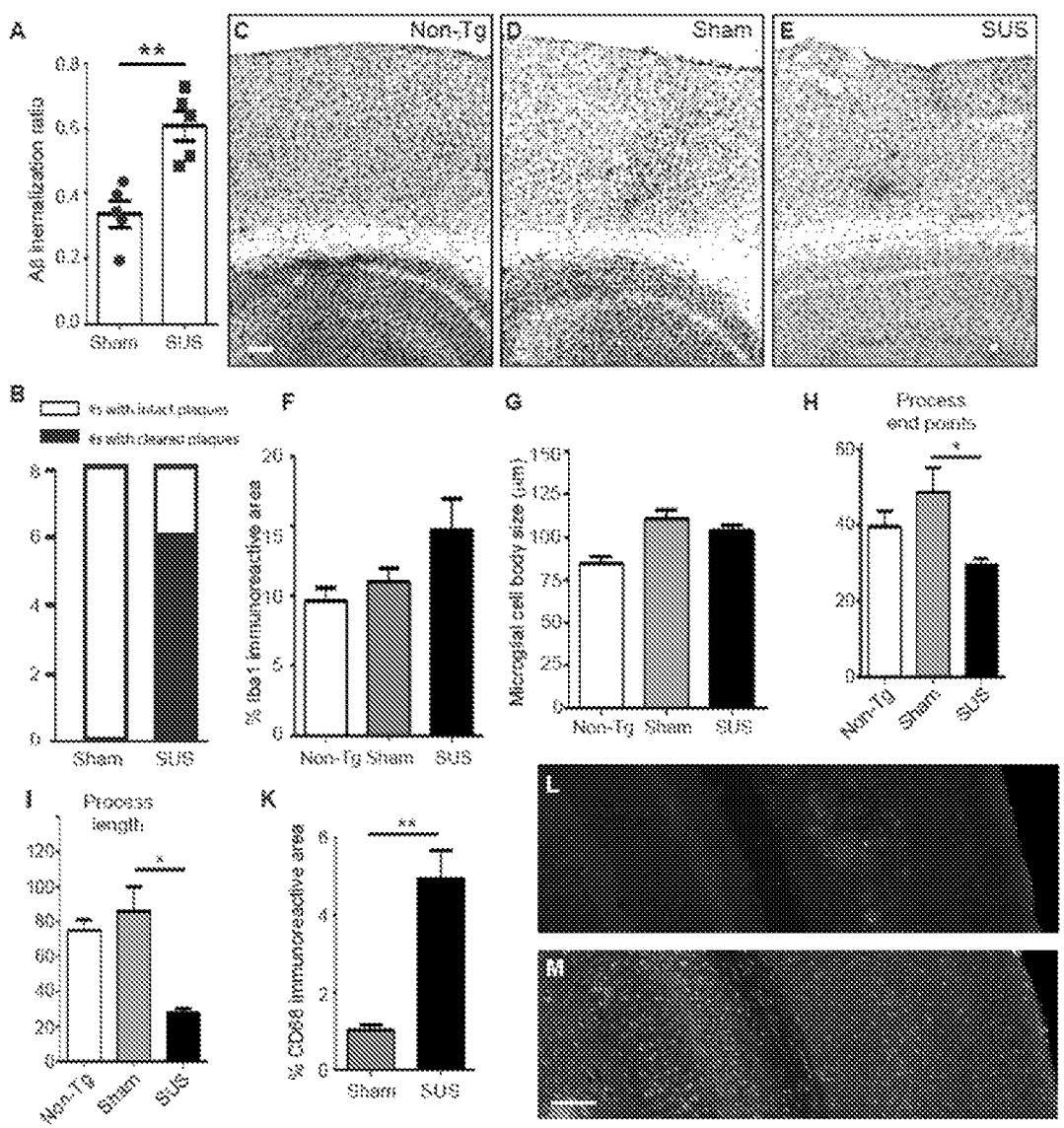
FIG. 8. Altered morphology after ultrasound but unaltered numbers of microglia in SUSed mice. (A) A two-fold increase in microglia-internalized Aβ was observed in SUSed compared to sham-treated brains (unpaired t-test, P=0.002). (B) Confocal analysis of Aβ and CD68 reveals that % SUSed mice and % sham-treated mice had 'cleared plaques' in cortical areas, with Aβ being almost completely within microglial lysosomes (Fisher's exact test, P=0.007, n=8 per group, with four sections analyzed in each case). Sections of Non-Tg (C), sham-treated APP23 (D) and SUSed APP23 mice (E) stained with the microglial marker Iba1. (F) The microglial surface area does not differ between the three groups. (G) There is also no difference in the size of the microglial cell bodies between the three groups. (H,I) A skeleton analysis in which both the summed microglial process endpoints (H) and the summed process length (I) were normalized per cell showing that microglia in the SUSed group are more activated. (K-M) This is also reflected by the fivefold increase in the surface area of CD68 immunoreactivity (t-test, P=0.001) (K), a marker of microglial/macrophage lysosomes, in SUSed (M) compared with sham-treated APP23 mice (L). Scale bars: C-E, L,M=100 μm.

We next sought to determine whether microglia in SUS-treated compared to sham-treated APP23 mice differed in other characteristics using sham-treated non-Tg littermates as control. Using the microglial cytoplasmic marker Iba1 (ionized calcium binding adaptor molecule 1) (FIG. 8, C to E), we first determined the total microglial surface area, but we did not find differences between the three groups (t test) (FIG. 8F); there was also no difference in the size of microglial cell bodies (t test) (FIG. 8G). Resting microglia have highly branched extensions unlike activated phagocytic microglia. To quantify the extent of branching, after staining with the activated microglial marker Iba1, we converted the images to binary images that were then skeletonized (to obtain the most accurate tree geometry possible). In this analysis, both the summed microglial process endpoints and the summed process length were normalized per cell using the Analyze Skeleton plugin in ImageJ (National Institutes of Health) (FIGS. 8H and I). This showed that microglia in the SUS-treated group were more activated, a finding that was also reflected by a fivefold increase in the area of immunoreactivity for CD68 (t test, P=0.001), a specific marker of microglial and macrophage lysosomes (FIG. 8, K to M).

Figure 10:
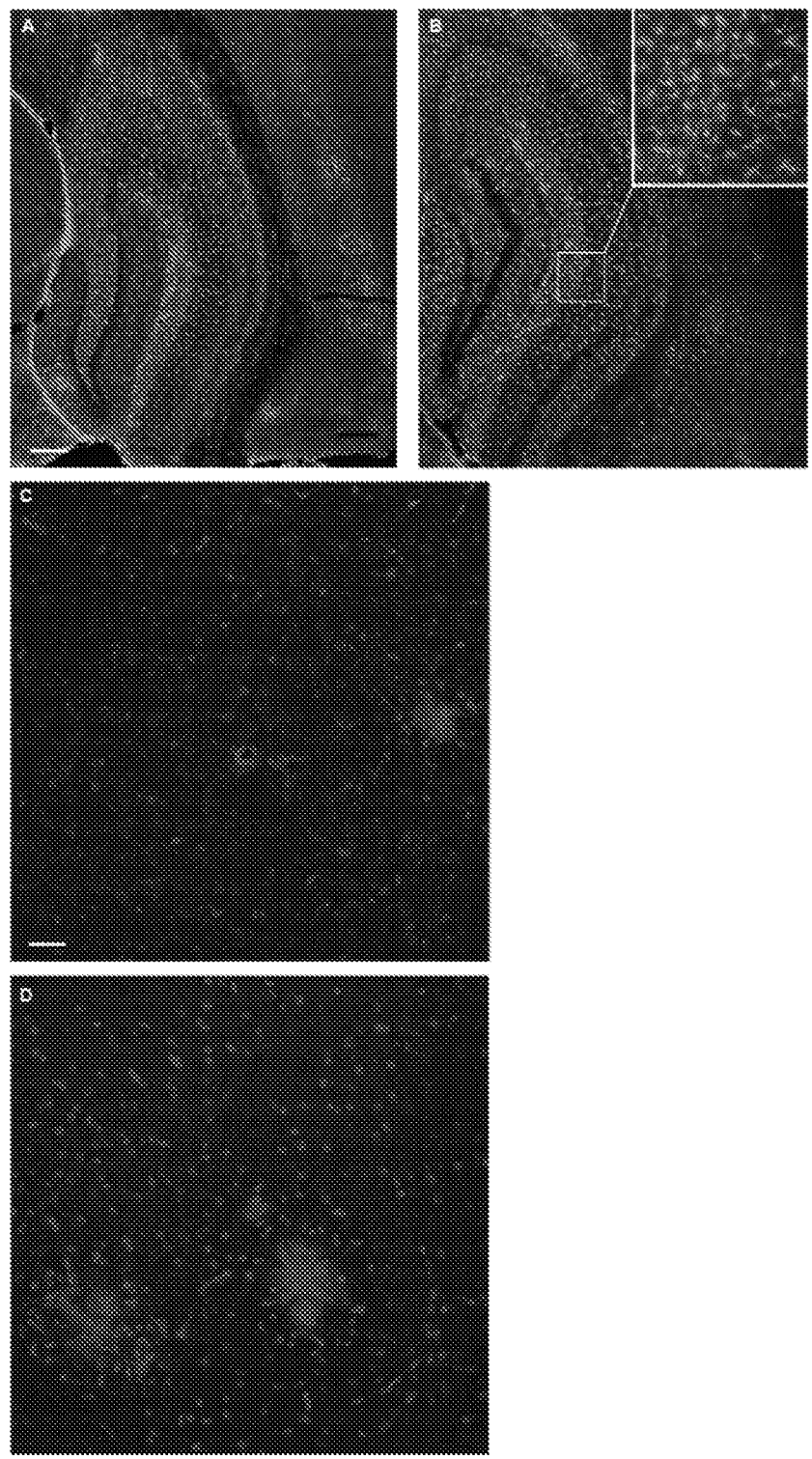
FIG. 10. Analysis of SUS-treated mice for inflammatory markers. (A,B) Immunoreactivity (percentage immunoreactive area) for the astrocytic marker GFAP is increased in APP23 compared to Non-Tg mice, but there is no difference between sham-treated (A) and SUS-treated APP23 mice (B). (C,D) NFkB-positive nuclei as a marker of excessive, chronic inflammation are absent in wild-type mice. In APP23 mice NFkB-positive nuclei are low in numbers and are confined to plaques, with no obvious difference between SUS-treated (C) and sham-treated APP23 mice (D). (Blue, DAPI; green, Iba1; red, nuclear NFkB). Scale bars: 200 µm.

Finally, we determined whether SUS up-regulated inflammatory markers associated with tissue damage. We first assessed the astrocytic marker GFAP (glial fibrillary acidic protein) and found an increased immunoreactivity (percentage of immunoreactive area) in APP23 compared to non-Tg mice, but no difference between SUStreated and sham-treated APP23 mice (FIGS. 10, A and B). We also investigated the nuclear localization of the transcription factor NF-kB (nuclear factor kB), a marker of excessive, chronic inflammation. NF-kB-positive nuclei were absent in wild-type mice. In APP23 mice, they were confined to plaques, but we did not observe differences between SUS-treated and sham-treated animals (FIGS. 10, C and D). Together, our analysis suggested that SUS treatment did not lead to damaging inflammation.

Example 2

Study Design.

The study aimed to investigate how scanning ultrasound treatment (SUS) would affect Aβ levels, plaque load, microglial phagocytosis of Aβ and spatial memory. To this end, we gave 12-13 month-old male APP23 SUS treatment or sham treatment for a total duration of the experiment of six weeks. Using histological methods, Western blotting, ELISA and confocal microscopy we measured the effect of SUS treatment on amyloid pathology. Mice were randomly assigned to treatment groups. The treatment condition was kept blinded until the analysis. All animals were included in the analysis. Sample sizes were chosen based on previous experience and on the basis of studies of this type conducted by others.

Animal Models and Ethics.

Hemizygous male APP23 mice on a C57BL/6J background and their non-transgenic littermates were treated once a week for four weeks with Scanning Ultrasound (SUS), or were sham treated. APP23 mice express hAPP751 with the Swedish double mutation under control of the murine Thy1.2 promoter (C. Sturchler—Pierrat et al., Proc Natl Acad Sci USA 94, 13287 (1997)). The mice were 12-13 month-old at the start of treatment. APP23 mice of this age are characterized by pronounced mature amyloid plaques, mainly in the cortex, as well as associated memory deficits. Wild-type littermates of the APP23 mice were also tested in the Y maze. For sham treatment, mice received all injections and were placed under the ultrasound transducer, but no ultrasound was emitted. After the four-week treatment period the mice underwent behavioural testing in a two-week period in which they were not treated. Following this, mice had one more ultrasound treatment and were sacrificed four days later. Animal experimentation was approved by the Animal Ethics Committee of the University of Queensland (approval number QBI/027/12/NHMRC).

SUS Equipment.

An integrated focused ultrasound system was used (Therapy Imaging Probe System, TIPS, Philips Research)

(R. Seip et al., IEEE Trans Biomed Eng 57, 61 (2010)). The system consisted of an annular array transducer with a natural focus of 80 mm, a radius of curvature of 80 mm, a spherical shell of 80 mm with a central opening of 31 mm diameter, a three-dimensional (3D) positioning system, and a programmable motorized system to move the ultrasound focus in the x and y planes to cover the entire brain area. A coupler mounted to the transducer was filled with degassed water and placed on the head of the mouse with ultrasound gel for coupling to ensure propagation of the ultrasound to the brain. The focal zone of the array was an ellipse of approximately 1.5 mm×1.5 mm×12 mm.

Antibodies and Reagents.

Antibodies to Aβ peptide epitope 1-16 (6E10) and 17-24 (4G8) were from Covance. Antibodies to CD68 were from AbD Serotec (MCA195TT) and to GAPDH from Millipore. Secondary antibodies were from Invitrogen, Cell Signaling and Dako. The human Amyloid-β42 ELISA kit was from Millipore (EZH542). Total protein levels were assayed with a BCA kit from Pierce (23227). Chemical reagents were from Sigma.

Production of Microbubbles.

Lipid-shelled microbubbles with an octafluoropropane core were manufactured and characterized in-house. A 1:5:2:1 ratio of PEG6000, distearoyl-phosphatidylcholine, distearoylphosphatidylethanolamine, and pluronic F68 were dissolved in a 0.9% solution of sodium chloride. The solution was added to glass HPLC vials and the air was removed and replaced with octafluoropropane gas to fill the headspace of the vial (Arcadophta). On the day of use, vials were heated to 37° C. and then shaken in a dental amalgamator for 40 s at 4,000 rpm. The concentration and size of the microbubbles was examined under a microscope and found to be 1-5×$10^7$ microbubbles/ml with a size range of 1-10 μm, and a mean diameter of 4 μm (data not shown).

SUS Application.

Mice were anesthetized with zoletil (20 mg/kg) and xylazine (10 mg/kg) and the hair on the head was shaved and depilated. Mice were injected retroorbitally with 1 μl/g body weight of microbubble solution and then placed under the ultrasound transducer with the head immobilized. (Intravenous injections were also tested but proved less efficacious due to the small tail veins of the mice.) Parameters for the ultrasound delivery were 0.8 MPa peak rarefactional pressure, 10 Hz pulse repetition frequency, 10% duty cycle, and a 6 s sonication time per spot. The motorized positioning system moved the focus of the transducer array in a grid with 1.5 mm between individual sites of sonication so that ultrasound was delivered sequentially to the entire brain.

Monitoring Blood-Brain Barrier Opening and Damage to Brain Tissue.

To determine successful opening of the blood-brain barrier (BBB), 4 ml/kg of a 2% solution of Evans blue (EB) dye in 0.9% NaCl was injected together with a 1 μL/g dose of the microbubbles and SUS or sham treatment was performed as described above. After 30 min the mice were deeply anesthetized and transcardially perfused with phosphate buffered saline (PBS) followed by 4% paraformaldehyde (PFA) and photographed under a stereo microscope (Carl Zeiss). EB is >99% bound to albumin in the blood and is BBB impermeable. In addition, we found that SUSing increased the permeability of the BBB to albumin and mouse IgG by immunofluorescence on sections (data not shown). To determine damage, sections from SUS-treated mice were stained with hematoxylin and eosin to assess erythrocyte extravasation and tissue damage, as well as with cresyl violet (Nissl staining) to assess damaged 'dark' neurons.

Tissue Processing.

Mice were deeply anaesthetized with pentobarbitone before being perfused with 30 ml of ice-cold PBS. The brains were dissected from the skull and cut along the midline. The left hemisphere was fixed in 4% wt/vol PFA for 24 hours, cryoprotected in 30% sucrose and sectioned coronally at 40 μm thickness on a freezing sliding microtome. A one-in-eight series of sections was stored in PBS with sodium azide at 4° C. until staining. The right hemisphere of the brain was frozen in a dry ice/ethanol slurry and stored at −80° C. until used for biochemical analysis.

Assessment of Amyloid Plaque Load.

A one-in-eight series of coronal brain sections were cut at 40 μm thickness on a microtome. An entire series of sections was processed for Campbell-Switzer silver staining (D. R. Thal, U. Rub, M. Orantes, H. Braak, Neurology 58, 1791 (2002)) using a protocol available online at http://www.neuroscienceassociates.com/Documents/Publications/campbell-switzer_protocol.htm. For plaque counting, an entire one-in-eight series of sections were stained using the Campbell-Switzer method and all sections −0.85 mm to −2.8 mm from bregma were analyzed (8-10 sections per mouse) after being photographed at 16× magnification on a bright-field slide scanner. Plaque load in the cortex was obtained by the particle analysis plugin of ImageJ (NIH) on coded images of sections using the area fraction method.

Spinning Disk Confocal Microscopy and 3D-Rendering.

Confocal images were acquired using a spinning disk confocal head (CSU-W1, Yokogawa) coupled to a fully motorized inverted Zeiss Axio Observer Z1 microscope equipped with a 20× 0.8NA Plan-Apochromat air objective, a 100× 1.4NA Plan-Apochromat oil objective (Carl Zeiss) and an ORCA-Flash4.0 sCMOS camera (Hamamatsu) controlled by Slidebook (v5.5; Intelligent Imaging Innovations, Inc.).

Each 3D image stack consisted of image planes of 2048×2048 pixels (640×640 μm at 20× and 128×128 μm at 100×) that were separated by 1.2 μm and 0.4 μm for 20× and 100×, respectively, and acquired throughout the tissue section starting at the slide. Exposure times (100-800 ms) were maintained consistently for each marker across all experiments avoiding any incidence of pixel saturation.

Microglia (CD68-positive) were identified using automatic segmentation in Imaris (Bitplane). The 3D surfaces of microglia were used to mask Aβ labelling such that the volume of internalized Aβ could be determined. 3D rendering of plaques was created using 3D contouring tools in Imaris. For evaluation of the proportion of Aβ contained within microglial lysosomes, five sham-treated mice and five SUSed mice were analysed and differences were tested with a t-test.

Protein Extraction.

We performed a serial extraction to obtain fractions enriched for extracellular and a Triton-soluble fraction proteins as described elsewhere (S. Lesne et al., Nature 440, 352 (2006)). The forebrain of the right hemisphere was placed in four times weight/the volume of buffer containing 50 mM Tris-HCl, pH 7.6, 0.01% NP-40, 150 mM NaCl, 2 mM EDTA, 0.1% SDS, 1 mM phenylmethanesulfonyl fluorid (PMSF), and Complete (Roche) protease inhibitors. The tissue was dissociated with a syringe and a 19-gauge needle and the solution centrifuged at 800×g for 10 min to extract soluble extracellular proteins. Triton soluble and intracellular proteins were obtained by homogenizing the intact cell pellet in four volumes of 50 mM Tris-HCl, pH 7.4, 150 mM NaCl, 1% Triton X-100 and centrifuging for 90 min at 16,000×g. Total protein concentration was determined by BCA assay (Pierce). All extraction steps took place at 4° C. and aliquots of the samples were stored at −80° C. until use.

Western Blotting.

40 μg each of extracellular-enriched and Triton-soluble proteins were separated on 10-20% Tris-Tricine gels (Bio-Rad) and transferred to nitrocellulose membranes. Membranes were microwaved on a high setting for 30 s, and stained briefly in Ponceau-S to check transfer and equal loading. Membranes were then blocked in PBS containing Odyssey blocking reagent (Li-cor) and incubated overnight in a 1:2,000 dilution of 6E10 and 4G8 antibody (Covance). For the loading control, rabbit anti-GAPDH antibody (1:2,000, Millipore) was used. Membranes were then blotted with anti-mouse IgGIR680 and anti-rabbit IgG-IR800 fluorescent secondary antibodies (Li-cor) and imaged on a Li-cor Odyssey scanner with detection settings of intensity 4.0 for the 700 channel and 0.5 intensity for the 800 channel. Signals from detected bands were quantified with Image Studio software (Li-cor).

ELISA.

For detection of Aβ by ELISA we quantified levels of Aβ1-42 in the Triton soluble fraction, using ELISA kits from Millipore (EZH542).

Behavioural Testing.

The Y-maze was made of clear Plexiglas and had three identical arms (40×9×16 cm) 120° apart. The centre platform was a triangle with 9 cm side length. The room was illuminated by 70 lux. Mice were habituated to the testing room and the apparatus 24 h prior to testing by being in the maze for 5 min. On the day of testing mice were placed in one of the arms and allowed to explore the maze for 8 min. Arm entry was defined as having all four limbs inside one of the arms. Mice were videotaped and the videos were analyzed blind. The maze was cleaned with 70% ethanol between animals. The sequence of arm entries was used to obtain a measure of alternation, reflecting spatial working memory. The percentage alternation was calculated by the number of complete alternation sequences (ABC, BCA, CAB) divided by the number of alternation opportunities (total arm entries minus two).

Statistics.

Statistics was done with the Prism 6 software (GraphPad Software, USA). Values are always reported as mean±standard error. One-way ANOVA with Dunnett's post-hoc test was used for three groups, and unpaired t-test was used to compare two groups. Where there were significant differences in variance between groups we applied Welch's correction.

Behavioral Testing—Active Place Avoidance (APA) Test.

The APA task is a test of hippocampus-dependent spatial learning. Mice (APP23 mice and non-transgenic 9 littermate controls) were tested over five days in a rotating elevated arena (Bio-Signal group) that had a grid floor and a 32 cm high clear plastic circular fence enclosing a total diameter of grid of 77 cm. High-contrast visual cues were present on the walls of the testing room. The arena and floor was rotated at a speed of 0.75 rpm and a 500 ms, 60 Hz, 0.5 mA mild shock was delivered through the grid floor when the animal entered a 60 degree shock zone, and every 1,500 ms until the animal left the shock zone. The shock zone was maintained at a constant position in relation to the room. Recorded tracks were analyzed with Track Analysis software (Bio-Signal group). A habituation session was performed 24 h before the first training session in which animals were placed in the rotating arena for 5 min to explore but the mice did not receive any shocks during this period. After this initial testing APP23 mice were divided into two groups with mice matched so that the performance of the two groups of mice on day four of the task was the same. Four training sessions were held on consecutive days, one per day with a duration of 10 min. Following a 7 week-period of treatment in which the mice were given SUS or sham treatment (in which the sham mice received all injections but ultrasound was not applied), they were retested in the task (reversal learning). For retesting the shock zone was switched to the opposite side of the arena and the visual cues were changed but mice were tested in the same room. The number of shocks delivered to the SUSed APP23 mice, sham-treated APP23 mice, and sham-treated wild-type mice were compared over the days of testing. As an additional measure we broke the 10 min interval into two 5 min intervals, the first a measure of long-term memory and the second of working/short-term memory. Data was analyzed with a Two-Way ANOVA with day of testing as a within subjects factor and simple effects of group tested with Fisher's LSD post-hoc test.

Behavioral Testing—Novel Object Recognition (NOR) Test.

Mice were also tested in the NOR test. A Y-shaped arena made of white Perspex (30 cm height×16 cm length×8 cm wide) was used. Mice were placed in a start arm and the other arms contained the objects. A camera recorded the mice and Ethovision XT was used to analyze the time the mouse spent investigating less than 2 cm from the object with its nose pointed in the direction of the object. Between each trial the maze was thoroughly cleaned with paper towel and 70% ethanol. For two days prior to the test session mice underwent habituation to the Y shaped maze for 8 min each without any objects in the arms. On the third day a sample phase was followed by a choice phase. In the sample phase two identical copies of an object was placed at the end of two arms. The mice explored the objects for 8 min. Following a 30 min delay in which the animal was placed back in its home cage, a choice phase was carried out in which the objects were replaced by a third identical copy of one of the objects and a novel object to which the mice had not been exposed. The choice phase was 4 min in duration. Times when an animal climbed on an object were not counted. Which objects were sample and novel objects and in which arm the novel object was placed in were counterbalanced within and across groups. We calculated the preference for the novel object as the total time spent exploring the novel object subtracted from the time spent exploring the familiar object. Differences between groups were assessed by Student's t-test. We also calculated a discrimination ratio, by dividing this measure by the total time spent exploring both objects.

Microglial Uptake.

BV-2 microglia cells (kindly provided by Dr Trent Woodruff, University of Queensland) were maintained in DMEM containing 1% fetal bovine serum, non-essential amino acids and antibiotics. Cells were passaged when 80% confluent and a passage number of 10-15 was used for the experiments. For phagocytosis studies, cells were plated at a density of 30,000 cells per chamber in eight well-tissue culture chamber slides (Sarstedt). Aβ42 biotinylated at the N-terminus (JPET) was dissolved in DMSO and then diluted to a 1 mg/ml concentration in PBS and aggregated at 37° C. for 7 days to obtain fibrillar Aβ (fAβ42). Cells grown in the chamber wells were treated with 10 mg/ml human serum albumin (Sigma) in normal medium for 24 h or with normal cell medium alone (control). As a negative control for phagocytosis, the actin polymerization inhibitor cytochalasin D was added at a 5 μM concentration 1 h prior to the addition of fAβ42. Cells were then treated with 2.5 μg/ml fAβ42 for 60 min and then washed twice with normal medium and then fixed with 4% paraformaldehyde for 20 min. Cells were permeabilized by adding 0.1% Triton X-100 and blocked with 1% bovine serum albumin for 1 h, before being incubated with the anti-LAMP2 (lysosomal-associated membrane protein 2) antibody (1:500, Sigma) overnight at 4° C. After washing with PBS, cells were incubated with Alexafluor 594-conjugated streptavidin to label biotinylated AR (1:1000, Invitrogen) for 1 h at room temperature and then stained with DAPI and cover-slipped with fluorescent mounting medium (Vectashield). Under confocal microscopy, three or four areas containing more than 100 cells in total were randomly chosen based on DAPI staining. Numbers of microglia containing phagozytosed fAβ42 were determined by counting the number of cells containing Alexafluor 594-labeled fAβ42 within LAMP2 positive areas and expressed as a percentage of the total number of cells counted. Data are representative of two experiments and expressed as mean±standard error of the mean (SEM).

Microglia Skeleton Analysis.

A skeleton analysis was applied to quantify microglial morphology in images obtained from fixed brains as described (5). In brief, 40 μm sections were stained with Iba1 using the nickel/DAB method. Two images from auditory cortex overlying the dorsal hippocampus (an area rich in plaques) were each converted to binary images and then skeletonized using the Analyze Skeleton plugin by ImageJ. The number of summed microglial process endpoints and summed process length normalized to the number of microglia were determined.

The Examples herein demonstrate that repeated scanning (SUSing) of the entire brain is sufficient to markedly ameliorate the pathology of Aβ-depositing mice, histologically, biochemically and behaviorally.

In conclusion, this study highlights the potential of SUSing as a viable therapeutic approach for AD, and other diseases with protein aggregation, such as frontotemporal dementia and motor neuron disease.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method of improving cognitive function in an individual with impaired cognitive function, comprising:
    identifying a region of the brain of the individual to be treated with acoustic energy, wherein the region is the entire brain or an entire hemisphere thereof; and
    applying a dose of the acoustic energy in the form of focused ultrasound to substantially the entire brain or to substantially the entire hemisphere thereof in a single treatment;
    wherein applying the acoustic energy is effective to provide conditions that result in an increase in permeability of the brain's blood-brain barrier and improve cognitive function in the individual, and
    wherein a therapeutic agent is not administered.

2. The method according to claim 1, wherein identifying the region of the brain includes determining a volume of the brain on the basis of symptoms displayed by the individual.

3. The method according to claim 2, wherein the symptoms displayed by the individual are observable or biochemically detectable symptoms.

4. The method according to claim 1, wherein identifying the region of the brain includes determining a volume of the brain on the basis of a known association with a neurodegenerative disease.

5. The method according to claim 4, wherein the neurodegenerative disease is associated with protein oligomers, aggregates or deposits.

6. The method according to claim 1, wherein identifying the region of the brain includes determining a volume of the brain including a volume surrounding a site having extracellular protein in a pathogenic form.

7. The method according to claim 6, wherein the pathogenic form of the extracellular protein is in the form of an oligomer, an aggregate, or a deposit.

8. The method according to claim 1, wherein the method further includes determining a scanning path along which the acoustic energy is to be applied.

9. The method according to claim 8, wherein the method further includes determining a plurality of discrete application sites for application of the acoustic energy along the scanning path.

10. The method according to claim 1, wherein applying the dose of the acoustic energy to the region includes providing the acoustic energy continuously, or at application sites, along a scanning path.

11. The method according to claim 1, wherein applying the dose of the acoustic energy includes applying the acoustic energy to a plurality of discrete application sites or one or more extended application sites.

12. The method according to claim 1, wherein the acoustic energy is applied transcranially at a pressure greater than 0.4 MPa.

13. The method according to claim 1, wherein the application of the acoustic energy is not image-guided.

14. The method according to claim 1, wherein applying the acoustic energy is effective to provide conditions for activating microglia.

15. The method according to claim 1, wherein the focused ultrasound is applied with a mechanical index of between 0.1 and 2.

16. The method according to claim 15, wherein the focused ultrasound is applied with a duty cycle of about 0.1% to about 50%.

17. The method according to claim 15, wherein the focused ultrasound is applied with a pulse length of between about 1 to about 100 milliseconds.

18. The method according to claim 15, wherein the focused ultrasound is applied with burst mode repetition frequencies of between about 10 Hz to 100 kHz.

19. The method according to claim 15, wherein the focused ultrasound is applied with a focal spot size of about 1 mm to 2 cm axial width.

20. The method according to claim 15, wherein the focused ultrasound is applied with a focal spot length of about 1 cm to about 15 cm.

21. The method according to claim 20, wherein the focused ultrasound is applied with a focal spot length of about 1 cm to 5 cm.

22. The method according to claim 15, wherein the focused ultrasound is applied with a duty cycle of about 1% to about 5%.

23. The method according to claim 15, wherein the focused ultrasound is applied with a pulse length of between about 1 to 20 milliseconds.

24. The method according to claim 15, wherein the focused ultrasound is applied with burst mode repetition frequencies of between about 10 Hz to 100 Hz.

25. The method according to claim 15, wherein the focused ultrasound is applied with a focal spot size of about 1 mm to 0.5 cm axial width.

26. The method according to claim 1, wherein the individual is identified as having a condition selected from the group consisting of Alzheimer's Disease, dementia with Lewy bodies, Parkinson's disease, frontotemporal lobar degeneration and British and Danish familial dementia.

27. The method according to claim 1, wherein the individual is identified as having a condition involving the presence of a pathogenic protein selected from the group consisting of amyloid beta, amyloid fragments, amyloid precursor protein, amyloid precursor protein fragments and British peptide.

28. The method of claim 1, further comprising treating the subject with an additional acoustic energy treatment, wherein the additional treatment comprises applying a dose of the acoustic energy in the form of focused ultrasound to substantially the entire brain or to substantially the entire hemisphere thereof in a single treatment.

29. A method of improving cognitive function in an individual with a neurodegenerative disease characterized by aggregation of a pathological protein, the method comprising:
applying a dose of acoustic energy in the form of focused ultrasound to sites within a region of the brain associated with the neurodegenerative disease,
wherein the region is the entire brain or an entire hemisphere thereof and the acoustic energy is applied to substantially the entire brain or to substantially the entire hemisphere thereof in a single treatment,
wherein applying the acoustic energy to at least some of the sites does not direct the acoustic energy to deposits of the pathological protein,
wherein applying the acoustic energy is effective to provide conditions that result in an increase in permeability of the brain's blood-brain barrier and improve cognitive function in the individual, and
wherein a therapeutic agent is not administered.

30. The method according to claim 29, wherein a location of deposits of the pathological protein in the brain of the individual has not been previously determined by imaging.

31. The method according to claim 29, wherein the sites are substantially uniformly distributed throughout the region.

32. The method of claim 29, further comprising treating the subject with an additional acoustic energy treatment, wherein the additional treatment comprises applying a dose of the acoustic energy in the form of focused ultrasound to substantially the entire brain or to substantially the entire hemisphere thereof in a single treatment.

33. A method of improving cognitive function in an individual with impaired cognitive function, comprising:
identifying a region of the brain of the individual to be treated with acoustic energy, wherein the region is the entire brain or an entire hemisphere thereof;
administering a microbubble agent to the individual; and
applying a dose of the acoustic energy in the form of focused ultrasound to substantially the entire brain or to substantially the entire hemisphere thereof in a single treatment,
wherein a therapeutic agent other than the microbubble agent is not administered, and
wherein applying the acoustic energy is effective to provide conditions that result in an increase in permeability of the brain's blood-brain barrier and improve cognitive function in the individual.

34. The method of claim 33, further comprising treating the subject with an additional acoustic energy treatment, wherein the additional treatment comprises applying a dose of the acoustic energy in the form of focused ultrasound to substantially the entire brain or to substantially the entire hemisphere thereof in a single treatment.

35. A method of improving cognitive function in an individual with a neurodegenerative disease characterized by aggregation of a pathological protein, comprising:
administering a microbubble agent to the individual; and
applying a dose of acoustic energy in the form of focused ultrasound to sites within a region of the brain associated with the neurodegenerative disease, wherein the region is the entire brain or an entire hemisphere thereof and the acoustic energy is applied to substantially the entire brain or to substantially the entire hemisphere thereof in a single treatment,
wherein applying the acoustic energy to at least some of the sites does not direct the acoustic energy to deposits of the pathological protein,
wherein a therapeutic agent other than the microbubble agent is not administered, and
wherein applying the acoustic energy is effective to provide conditions that result in an increase in permeability of the brain's blood-brain barrier and improve cognitive function in the individual.

36. The method of claim 35, further comprising treating the subject with an additional acoustic energy treatment, wherein the additional treatment comprises applying a dose of the acoustic energy in the form of focused ultrasound to substantially the entire brain or to substantially the entire hemisphere thereof in a single treatment.

* * * * *